US008710010B2

(12) United States Patent
Van Den Nest et al.

(10) Patent No.: US 8,710,010 B2
(45) Date of Patent: Apr. 29, 2014

(54) PEPTIDES USEFUL IN THE TREATMENT AND/OR CARE OF SKIN, MUCOUS MEMBRANES, SCALP AND/OR HAIR AND THEIR USE IN COSMETIC OR PHARMACEUTICAL COMPOSITIONS

(75) Inventors: Wim Van Den Nest, Vilanova i la Geltrú (ES); Nuria Almiñana Domenech, Barcelona (ES); Juan Cebrián Puche, Barcelona (ES); Cristina Carreño Serraïma, Barcelona (ES)

(73) Assignee: Lipotec, S.A., Gava Barcelona (ES)

( * ) Notice: Subject to any disclaimer, the term of this patent is extended or adjusted under 35 U.S.C. 154(b) by 231 days.

(21) Appl. No.: 13/122,435

(22) PCT Filed: Oct. 2, 2009

(86) PCT No.: PCT/EP2009/007075
§ 371 (c)(1),
(2), (4) Date: Apr. 26, 2011

(87) PCT Pub. No.: WO2010/037553
PCT Pub. Date: Apr. 8, 2010

(65) Prior Publication Data
US 2011/0195102 A1 Aug. 11, 2011

Related U.S. Application Data

(60) Provisional application No. 61/102,576, filed on Oct. 3, 2008.

(30) Foreign Application Priority Data

Oct. 3, 2008 (ES) .................................. 200802818

(51) Int. Cl.
*A61K 38/00* (2006.01)
*A61P 17/00* (2006.01)

(52) U.S. Cl.
USPC ........................................ 514/18.6; 514/18.8

(58) Field of Classification Search
None
See application file for complete search history.

(56) References Cited

U.S. PATENT DOCUMENTS

| 6,497,862 B2 | 12/2002 | Oku et al. |
| 2002/0192171 A1 | 12/2002 | Li et al. |
| 2007/0031516 A1 | 2/2007 | Garcia Anton et al. |
| 2007/0237735 A1 | 10/2007 | Denommee |

FOREIGN PATENT DOCUMENTS

| DE | 10237458 | 2/2004 |
| EP | 1129693 | 5/2001 |
| EP | 0955035 | 9/2004 |
| EP | 1611898 | 10/2008 |
| JP | 2001254274 | 9/2001 |
| WO | 02060953 | 8/2002 |

OTHER PUBLICATIONS

Khan Mh, et al., "Treatment of cellulite: Part II. Advances and controversies," J Am Acad Dermatol. Mar. 2010;62(3):373-84.*
Saeidnia S, "Antioxidants: Friends or foe in prevention or treatment of cancer: The debate of the century," Toxicol Appl Pharmacol. May 13, 2013. [Epub ahead of print]. 15 pages.*
International Search Report for PCT/EP2009/007075, Completed by the European Patent Office Jan. 28, 2010, 3 pages.
Schabb. Happi, May 1986, p. 84-86, "Impregnating Fabrics With Microcapsules."
Nelson. International Journal of Pharmaceutics 2002, vol. 242, p. 55-62, "Application of microencapsulation in textiles."
Wang. Journal of the American Chemical Society Feb. 21, 1973, vol. 95, No. 4, p. 1328-1333 "p-Alkoxybenzyl Alcohol Resin and P-Alkoxybenzyloxycarbonylhydrazide Resin for Solid Phase Synthesis of Protected Peptide Fragments."
Kullmann. The Journal of Biological Chemistry Issue of Sep. 10, 1980, vol. 255, No. 17, p. 8234-8238, " Proteases as Catalysts for Enzymic Syntheses of Opioid Peptides."
Berge et al. Journal of Pharmaceutical Sciences Jan. 1977, vol. 66, No. 1, p. 1-19, "Review Article, Pharmaceutical Salts."
Stewart et al. Solid Phase Peptide Synthesis 1984 second edition 1984, "The Chemistry of Solid Phase Peptide Synthesis.", All together 20 Pages.
Bodanszky et al. The Practice of Peptide Synthesis second edition 1984, "Activation and Coupling", All together 54 Pages.
Lloyd-Williams et al. Tetragedron 1993, vol. 49, No. 48, p. 11065-11133, "Tetrahedron Report No. 347, Convergent Solid-Phase Peptide Synthesis."
Greene et al. Protective Groups in Organic Synthesis third edition, 1999, "The Role of Protective Groups in Organic Synthesis.", All together 20 Pages.
Atherton et al. The Practical Approach Series 1989, All together 17 Pages, "Solid Phase peptide synthesis, a practical approach."
Matsueda et al. Peptides 1981, vol. 2, p. 45-50, "A p-Methylbenzhydrylamine Resin for Improved Solid-Phase Syntheis of Peptide Amides."
Barlos et al. Tetragedron Letters 1989, vol. 30, No. 30, p. 3947-3950, "Veresterung Von Partiell Geschutzten Peptid-Fragmenten Mit Harzen. Einsatz Von 2-Chlortritylchlorid Zur Synthese Von Leu 15—Gastrin I."
Albericio et al. J. Org. Chem. 1990, vol. 55, p. 3730-3743, "Preparation and Application of the 5-(4-(9-Fluorenylmethyloxycarbonyl)aminomethyl-3,5-dimethoxyphenoxy)- valeric Acid (PAL) Handle for the Solid-Phase Synthesis of C-Terminal Peptide Amides under Mild Conditions 1-3."
Kaiser et al. Anal. Biochem. 1970, vol. 34, pg. 595-598, "Color Test for Detection of Freee Terminal Amino Groups in the Solid-Phase Synthesis of Peptides."

(Continued)

*Primary Examiner* — Thomas Heard
(74) *Attorney, Agent, or Firm* — Fay Sharpe LLP

(57) ABSTRACT

Peptides with general formula (I): $R_1$-$AA_1$-$AA_2$-$AA_3$-$AA_4$-$R_2$ its stereoisomers, mixtures thereof, and its cosmetically or pharmaceutically acceptable saits, a method of preparation, cosmetic or pharmaceutical compositions containing them and their use for the treatment and/or care of conditions, disorders and/or pathologies of the skin, mucous membranes, scalp and/or hair.

18 Claims, No Drawings

(56) References Cited

OTHER PUBLICATIONS

Rink, Tetrahedron Letters 1987, vol. 28, No. 33, p. 3787-3790, "Solid-Phase Synthesis of Protected Peptide Fragements Using a Trialkoxy-Diphenyl-Methylester Resin."

Cebrian et al. International Journal of Cosmetic Science 2005, vol. 27, p. 271-278, "New anti-RNS and -RCS products for cosmetic treatment."

Joint Commussion on Biochemical Nomenclature Eur. J. Biochem. 1984, vol. 138, p. 9-37, "Nomenclature and Symbolism for Amino Acids and Peptides."

Liu et al. Molecular Aspects of Medicine 2003, vol. 24, p. 305-313, "Hydroxynonenal, toxic carbonyls, and Alzheimer disease."

Pegova et al. Comparative Biochemistry and Physiology Part B 2000, vol. 127, p. 443-446, "Hydrolysis of carnosine and related compounds by mammalian carnosinases."

Dweck. R.G. Harry Cosmeticology 8th edition, 2000, 27 Pages, "Botanicals in Cosmetics & Toiletries."

Barlos et al. Tetrahedron Letters 1989, vol. 30, No. 30, p. 3943-3946, "Darstellung Geschutzter Peptid-Fragmente Unter Einsatz Substituierter Triphenylmethyl-Harze."

Gottschalck et al. International Cosmetic Ingredient Dictionary and Handbook, 12th edition 2008, vol. 3, 14 Pages, "Biological Polymers and their Derivatives (Including salts, excluding gums, hydrophilic colloids and derivatives)."

Malcolm et al. Journal of Controlled Release 2004, vol. 97, p. 313-320, "Controlled release of model antibacterial drug from a novel self-lubricating silicone biomaterial."

Senol et al. CUTIS Feb. 1999, vol. 63, p. 107-111, "Body Odor in Dermatologic Diagnosis."

Uchida et al. The Journal of Biological Chemistry 1999, vol. 274, No. 4, p. 2234-2242, "Activation of Stress Signaling Pathway by the End Product of Lipid Peroxidation."

Uchida et al. The Journal of Biological Chemistry 1998, vol. 273, No. 26, p. 16058-16066, :Acrolein Is a Product of Lipid Peroxidation Reaction.

Christensen, Acta Chemica Scandinavica B 1979, vol. 33, p. 763-766, "A Qualitative Test for Monitoring Coupling Completeness in Solid Phase Peptide Synthesis Using Chloranil."

Hipler et al. Biofunctional Textiles and the Skin 2006, vol. 33, 10 Pages, "Current Problems in Dermatology."

Napoli May 24-27, 2006, 116 Pages, "The Maillard Reaction in Food and Medicine."

Remington, 21st edition, 2005, "The Science and Practice of Pharmacy." 60 Pages.

Smith et al. 1999, 5th edition, 111 Pages, "March's Advanced Organic Chemistry Reactions, Mechanisms, and Structure."

Lloyd-Williams et al. Chemical Approaches to the Synthesis of Peptides and Proteins 1997, 78 Pages, "Solid-Phase Peptide Synthesis."

Fauli. Treated Galenic Pharmacy 1993, "Pharmaceutical Technology", English translation of first paragraph, 8 Pages.

Haze et al. J. Invest Dermatol 2001, vol. 116, p. 520-524, "2-Nonenal Newly Found in Human Body Odor Tends to Increase with Aging."

Labows, Perfumer & Flavorist Aug./Sep. 1979, vol. 4, p. 12-17, "Human odors-what can they tell us?"

Aldini et al. Chem Med Chem 2006, vol. 1, p. 1045-1058, "Lipoxidation-Derived Reactive Carbonyl Species as Potential Drug Targets in Preventing Protein Carbonylation and Related Cellular Dysfunction."

Pullen et al. Biochemistry 1998, vol. 37, p. 11836-11845, "CD40—Tumor Necrosis Factor Receptor—Associated Factor (TRAF) Interactions: Regulation of CD40 Signaling through Multiple TRAF Binding Sites and TRAF Hetero-Oligornerization."

* cited by examiner

PEPTIDES USEFUL IN THE TREATMENT AND/OR CARE OF SKIN, MUCOUS MEMBRANES, SCALP AND/OR HAIR AND THEIR USE IN COSMETIC OR PHARMACEUTICAL COMPOSITIONS

CROSS-REFERENCE TO RELATED APPLICATION

This application is the U.S. national phase of PCT Appln. No. PCT/EP2009/007075 filed Oct. 2, 2009 which claims priority to Spanish application P200802818 filed Oct. 3, 2008 and claims the benefit of U.S. provisional application Ser. No. 61/102,576 filed Oct. 3, 2008, the disclosures of which are incorporated in their entirety by reference herein.

FIELD OF THE INVENTION

This invention relates to peptides capable of inhibiting the activity of Reactive Carbonyl Species (RCS) and to cosmetic and pharmaceutical compositions containing these peptides and their use in the treatment and/or care of skin, mucous membranes, scalp and/or hair, preferably for the treatment and/or care of said conditions, disorders and/or diseases of the skin, mucous membranes, scalp and/or hair which are the result of RCS generation.

BACKGROUND OF THE INVENTION

Cellular aging, especially the aging of skin cells, has been extensively studied. One of the most important factors in cellular aging is the formation and accumulation of free radicals within cells. Cellular aging is usually fought by protecting the skin by blocking mechanisms against UVA/UVB radiation and against reactive oxygen species (ROS) or oxygen free radicals, which are generated by exposure to sunlight and oxygen, their formation being catalyzed by pollutants and enhanced by the presence of traces of ozone. An important group of free radicals are the Reactive Carbonyl Species (RCS) generated in oxidative biological processes such as lipid peroxidation, which are one of the factors involved in accelerated skin aging, skin aging by UV radiation and erythema of the skin. In the context of this invention, the term "aging" refers to changes in the skin that occur with age (chronoaging) or sun exposure (photoaging) or environmental agents such as tobacco smoke, extreme cold conditions of weather or wind, chemical pollutants or pollution, and includes all external visible changes as well as those perceptible by touch, for example and without limitation thereto, the development of discontinuities in skin such as wrinkles, fine lines, cracks, irregularities or roughness, enlarged pores, loss of elasticity, loss of firmness, loss of smoothness, loss of recovery from deformation, sagging of the skin such as sagging of the cheeks, the appearance of bags under the eyes or the appearance of jowls, inter alia, changes in skin color such as spots, redness, dark circles, bags under the eyes or the emergence of hyperpigmented areas such as age spots or freckles, inter alia, abnormal differentiation, hypercornification, elastosis, keratosis, hair loss, appearance of orange-peel skin or cellulite, loss of the structure of collagen and other histological changes of the stratum corneum, the dermis, the epidermis, the vascular system, such as the emergence of spider veins or telangiectasia, or of the tissues close to the skin, inter alia.

At molecular level, the RCS are responsible for, among other processes, for DNA damage, degradation of proteasomes and alteration of intra and extracellular proteins [Degenhardt T P, Brinkmann-Frye S R, Thorpe S R and Baynes J. W. (1998) in *The Mailard Reaction in Foods and Medicine*, J. O'Brien, Nursten H E, Crabbe M J C and Ames J M, eds, pp 3-10, The Royal Society of Chemistry, Cambridge, UK]. These species include unsaturated aldehydes and the peroxidation of polyunsaturated fatty acids in the form of α aldehyde, β-unsaturated, harmful and toxic cells. Aldehydes are also formed in glycation reactions, and by the influence of different pollutants. Some of the major aldehydes formed by lipid peroxidation are malondialdehyde (MDA), acrolein, 4-hydroxy 2-nonenal (HNE), 2-nonenal (NE), glyoxal and methylglyoxal, formed by the influence of different pollutants, formaldehyde, acrolein and crotonaldehyde. These aldehydes, due to their electrophilic nature, are highly reactive with cellular nucleophiles such as glutathione, protein side chains of cysteine, lysine and histidine, and nucleic acids [Liu Q, Raina A K, Smith M A, Sayre L M and Perry G. (2003) "*Hydroxynonenal, toxic carbonyls, and Alzheimer disease*" Mol. Aspects Med 24:305-313]. These aldehydes not only degrade key components such as cellular DNA, but their effect is compounded because the proteins involved in the endogenous DNA repair mechanisms are also damaged, losing their functionality.

In particular, HNE is a metastable species, present in relatively high concentrations in biological tissues, which can easily spread from their place of origin and thus can propagate oxidative damage by acting as a secondary toxic messenger [Uchida K., Shiraishi M., Naito Y, Torii Y, Nakamura Y. and Osawa T. (1999) "*Activation of stress signaling pathways by the end product of lipid peroxidation. 4-hydroxynonenal is a potential inducer of intracellular peroxide production* "J. Biol Chem 274:2234-2242]. Acrolein, in turn, is an unwanted and unstable byproduct caused by overheated organic matter, and is present as a contaminant in the environment, for instance formed by the incomplete combustion of plastic and consumption of tobacco [Uchida K., Kanematsu M., Morimitsu Y, Osawa T., Noguchi N. and Niki E. (1998) "*Acrolein is a product of lipid peroxidation reaction. Formation of free acrolein and its conjugate with lysine residues in oxidized low density lipoproteins*, "J. Biol Chem 273:16058-16066]. In the natural protection mechanisms of cells the RCS are captured by certain scavenger substances in cells, such as glutathione, in order to avoid toxic or harmful effects on the cell, specifically damage to proteins and to cellular DNA. However, this scavenging of RCS cells by natural mechanisms does not occur properly when the cell is subjected to UV radiation; this circumstance is common, for example, in dermal cells. This alteration of the natural protection mechanisms also involves a decrease in the efficacy of DNA repair mechanisms, because the proteins involved in repair processes are damaged. Therefore, there is a need to assist the scavenging of the RCS in cells exposed to UV radiation. In this sense, the administration of sequestering substances has been suggested, in order to help catch these RCS to prevent degradation of cell proteins and DNA, essential components for cellular viability, as well as to enhance the efficacy of the DNA repair mechanisms. The scavenging will therefore reduce, delay and/or prevent symptoms of aging and/or photoaging.

A secondary effect of the treatment of cellulite with lipolytic agents is the rapid generation of fatty acid oxidation which ends up producing an increase in skin RCS. The toxic effect of these RCS causes premature aging of the treated skin, with a loss of elasticity that involves a persistent orange-peel appearance of the cellulite-affected area despite treatment. In this sense, the administration of sequestering substances has been suggested, in order to help scavenging these RCS to prevent their toxic or harmful effects. This scavenging will, therefore, improve the appearance of cellulite-affected skin and help prevent and/or treat cellulite.

There are several studies on the administration of certain substances with regard to their ability to scavenge RCS in cells, especially of carnosine and glycyl-histidyl-lysine (GHK) tripeptide. Carnosine has demonstrated an acceptable scavenging efficiency for two aldehydes, HNE and acrolein. However, carnosine has the drawback of being extremely labile to enzymatic action of specific enzymes such as carnosine [Pegova A., Abe H. and Boldyrev A. (2000) "*Hydrolysis of carnosine and related compounds by mammalian carnosine*" Comp. Biochem. Physiol. B. Biochem. Mol. Bio. 127:443-446]. Moreover, one of the direct decomposition products of carnosine is histidine, which can easily turn into histamine in the body and which is involved in allergic processes.

With regard to GHK tripeptide, some of its applications in its form of complexes with metals, especially copper, have been described. Thus it has been found that such complexes are involved in the regeneration and repair of some types of tissues in mammals, especially in the sense of accelerating wound repair, increasing re-epithelialization of the skin, increasing skin thickness, increasing the subcutaneous fat layer, increasing the size of hair follicles, curing stomach ulcers, etc. Its RCS scavenging efficiency has also been described, as well as the inhibition of cell death induced by exposure to RCS [Cebrian J., Messeguer A., Facino R M and Garcia Anton J. M. (2005) "*New anti-RNS and-RCS products for cosmetic treatment*" Int J. Cosmet. Sci 27:271-278], and its benefit as an adjunct in the treatment and/or prevention of cellulite [EP1611898 B1 Lipotec]. However, the chemical stability of tripeptide is low, rapidly degrading in solution, which requires an active stabilization protocol in cosmetic and pharmaceutical formulations.

Therefore, there is a need to find new RCS scavengers more stable than carnosine and GHK.

Body Odor

The nature of the odor emitted by the human body is influenced not only by endogenous factors such as genetic makeup or the pathologies presented by the human body, but also by factors such as lifestyle, food intake, smoking and bathing frequency [Labows J N (1979) "*Human odors*" Perf. 4:12-17 flavor, Senol M. and Fireman P. (1999) "*Body odor in dermatologic diagnosis*" Cutis 63:107-111]. Components of the scent given off by the human body have been identified, mostly volatile aldehydes formed from fatty acids and their esters secreted by various human organs and/or cells. The components of body odor are not constant throughout the different stages of life. Specifically, the smell of people of middle and advanced age is due mostly to aldehydes of unsaturated fatty acids such as 2-nonenal or 2-octenal, formed from 9-hexacedenoic acid, which is found primarily in the sebaceous secretions of people of middle and advanced age and is responsible for the unpleasant, fatty and rancid body odor that is associated with aging [S. Haze, Y. Gozu, S. Nakamura, Y. Kohno, K. Sawano, H. Ohta and K. Yamazaki (2001) "2-*Nonenal newly found in human body odor tends to increase with aging*," J. Invest. Dermatol. 116:520-524]. These α and β unsaturated aldehydes are Reactive Carbonyl Species (RCS) generated in the fat and skin during the process of lipid peroxidation incurred by fatty acids in situations of oxidative stress.

The cosmetics industry has employed various strategies for mitigating this odor, which are based on masking body odor with a fragrance or perfume or employing physical absorbents to prevent the dispersal of the scent. Neither of these strategies solves the problem of body odor as they do not inhibit the formation of odor per se and furthermore entail that, collaterally, the use of perfumes generates more aggressive odors when the different aromatic compounds are mixed or that the use of absorbents such as cyclodextrins or charcoal does not yield immediate results. A different strategy is based on inhibition of the generation of body odor and involves the use of antioxidants and/or antibacterial agents. These agents are effective in inhibiting the generation of odor, but it is known that their continued use can cause allergies.

Thus, there is a need for new substances capable of inhibiting body odor, specifically body odor caused by the generation of RCS and associated with aging. Patent application DE 102 37 458 A1 describes the use of carnosine as an inhibitor of body odor caused by the generation of RCS. Patent EP 0 955 035 B1 describes the use of antioxidants, lipoxygenase inhibitors and/or antibacterial agents with substances capable of masking body odor caused by the generation of RCS. Patent application JP 2001254274 A describes tissues functionalized with agents for inhibiting body odor caused by RCS. U.S. Pat. No. 6,497,862 B1 describes the use of trehalose and/or maltitol as agents for inhibiting body odor caused by the generation of RCS. GHK tripeptide and carnosine and their derivatives are the only peptides able to scavenge RCS and thus are potent anti-aging agents and inhibitors of body odor. However, these two peptides have the stability problems mentioned above.

Thus, there is a need for new effective peptides capable of scavenging RCS and solving the stability problems known in the state of the art.

DETAILED DESCRIPTION OF THE INVENTION

This invention provides a solution to the above problem. Surprisingly, the applicant of this invention has found that certain peptides, not derived from natural products, show significant efficacy in scavenging Reactive Carbonyl Species (RCS) and are therefore useful for the treatment and/or care of those conditions, disorders and/or diseases of the skin, mucous membranes, scalp and/or hair that result from the generation of RCS.

Definitions

To facilitate the understanding of this invention, the meanings of some terms as used in the context of the invention are included.

In this description, the abbreviations used for amino acids follow the rules of the Commission on Biochemical Nomenclature of the IUPAC-IUB specified in *Eur J. Biochem.* (1984) 138:9-37 and *J. Chem* (1989) 264:633-673.

Thus, for example, Gly represents $NH_2$—$CH_2$—COOH, Gly- represents $NH_2$—$CH_2$—CO—, -Gly represents —NH—$CH_2$—COOH and -Gly- represents —NH—$CH_2$—CO—. Therefore, the hyphen, which represents the peptide bond, eliminates the OH of the amino acid group 1-carboxyl (represented here in the conventional non-ionized form) when placed to the right of the symbol, and eliminates the H of the amino acid group 2-amino when placed to the left of the symbol; both modifications can be applied to the same symbol (see Table 1).

TABLE 1

| Symbol | Residue | Symbol | Residue |
|---|---|---|---|
| -Agl- | [structure: N-H, CH with NH₂ side chain, C=O] | -Ala- | [structure: N-H, CH with CH₃, C=O] |
| -Dpr- | [structure: N-H, CH with CH₂-NH₂, C=O] | -Dab- | [structure: N-H, CH with (CH₂)₂-NH₂, C=O] |
| -Orn- | [structure: N-H, CH with (CH₂)₃-NH₂, C=O] | -Lys- | [structure: N-H, CH with (CH₂)₄-NH₂, C=O] |
| -Asp- | [structure: N-H, CH with CH₂-COOH, C=O] | -Glu- | [structure: N-H, CH with (CH₂)₂-COOH, C=O] |
| -Pro- | [structure: pyrrolidine ring with C=O] | -His- | [structure: N-H, CH with CH₂-imidazole, C=O] |
| -Asn- | [structure: N-H, CH with CH₂-CONH₂, C=O] | | |

The abbreviation "Ac-" is used in this description to designate the acetyl group (CH$_3$—CO—) and the abbreviation "Palm-" is used to designate the palmitoyl group (CH$_3$—(CH$_2$)$_{14}$—CO—)

The term "non-cyclic aliphatic group" is used in this invention to encompass, for example and without limitation thereto, linear or branched alkyl, alkenyl and alkynyl groups.

The term "alkyl group" refers to a saturated group, linear or branched, which has between 1 and 24, preferably between 1 and 16, more preferably between 1 and 14, more preferably between 1 and 12, still more preferably 1, 2, 3, 4, 5 or 6 carbon atoms and is bound to the rest of the molecule by means of a single bond, including, for example and without limitation thereto, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl group and similar.

The term "alkenyl group" refers to a group, linear or branched, which has between 2 and 24, preferably between 2 and 16, more preferably between 2 and 14, more preferably between 2 and 12, still more preferably 2, 3, 4, 5 or 6 carbon atoms with one or more carbon-carbon double bonds; preferably with 1, 2 or 3 carbon-carbon double bonds, conjugated or unconjugated, which is bound to the rest of the molecule by means of a single bond, including, for example and without limitation thereto, vinyl, oleyl, linoleyl group and similar.

The term "alkynyl group" refers to a group, linear or branched, which has between 2 and 24, preferably between 2 and 16, more preferably between 2 and 14, more preferably between 2 and 12, still more preferably 2, 3, 4, 5 or 6 carbon atoms with one or more carbon-carbon triple bonds, preferably 1, 2 or 3 carbon-carbon triple bonds, conjugated or unconjugated, which is bound to the rest of the molecule by means of a single bond, including, for example and without limitation thereto, the ethynyl, 1-propynyl, 2-propynyl, 1-butynyl, 2-butynyl, 3-butynyl, pentynyl group, such as 1-pentynyl, and similar.

The term "alicyclyl group" is used in this invention to encompass, for example and without limitation thereto, cycloalkyl, cycloalkenyl or cycloalkynyl groups.

The term "cycloalkyl" refers to a saturated mono- or polycyclic aliphatic group which has between 3 and 24, preferably between 3 and 16, more preferably between 3 and 14, more preferably between 3 and 12, even more preferably 3, 4, 5 or 6 carbon atoms and is bound to the rest of the molecule by means of a single bond, including, for example and without limitation thereto, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, more preferably between 5 and 12, still more preferably 5 or 6 carbon atoms with one or more carbon-carbon double bonds, preferably 1, 2 or 3 carbon-carbon double bonds, conjugated or unconjugated, which is bound to the rest of the molecule by means of a single bond, including, for example and without limitation thereto, the cyclopent-1-en-1-yl group and similar.

The term "cycloalkynyl" refers to a non-aromatic mono- or polycyclic aliphatic group which has between 5 and 24, preferably between 5 and 16, more preferably between 5 and 14, more preferably between 5 and 12, still more preferably 5 or 6 carbon atoms with one or more carbon-carbon triple bonds, preferably 1, 2 or 3 carbon-carbon triple bonds, conjugated or unconjugated, which is bound to the rest of the molecule by means of a single bond, including, for example and without limitation thereto, the cyclohex-1-yn-1-yl group and similar.

The term "aryl group" refers to an aromatic group which has between 6 and 30, preferably between 6 and 18, more preferably between 6 and 10, more preferably 6 or 10 carbon atoms, comprising 1, 2, 3 or 4 aromatic rings, bound by means of a carbon-carbon bond or fused, including, for example and without limitation thereto, phenyl, naphthyl, diphenyl, indenyl, phenanthryl or anthranyl inter alia; or to an aralkyl group.

The term "aralkyl group" refers to an alkyl group substituted with an aromatic group which has between 7 and 24 carbon atoms and includes, for example and without limitation thereto, —$(CH_2)_{1-6}$-phenyl, —$(CH_2)_{1-6}$-(1-naphtyl), —$(CH_2)_{1-6}$-(2-naphty), —$(CH_2)_{1-6}$—CH(phenyl)$_2$ and similar.

The term "heterocyclyl group" refers to a hydrocarbon ring with 3-10 members, in which one or more atoms of the ring, preferably 1, 2 or 3 atoms of the ring, are an element other than carbon, for example nitrogen, oxygen or sulfur, and may be saturated or unsaturated. For the purposes of this invention, the heterocycle may be a monocyclic, bicyclic or tricyclic ring system, which may include fused ring systems; atoms of nitrogen, carbon or sulfur may optionally be oxidized in the heterocyclyl radical; the nitrogen atom can be optionally quaternized; and the heterocyclyl radical may be partially or completely saturated or be aromatic. With increasing preference, the term heterocyclyl refers to a ring with 5 or 6 member rings.

The term "heteroarylalkyl group" refers to an alkyl group substituted with a substituted or unsubstituted aromatic heterocyclyl group, the alkyl group having between 1 and 6 carbon atoms and the aromatic heterocyclyl group between 2 and 24 carbon atoms and 1 to 3 atoms other than carbon, including, for example and without limitation thereto, —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and similar.

As used in this technical area, there may be a degree of substitution on the groups defined above. Thus, there can be substitution in any of the groups of this invention. The references herein to substituted groups in the groups of this invention indicate that the specified radical may be substituted in one or more available positions by one or more substituents, preferably in 1, 2 or 3 positions, more preferably within 1 or 2 positions, still more preferably in 1 position. These substituents include, for example and without limitation thereto, $C_1$-$C_4$ alkyl; hydroxyl; $C_1$-$C_4$ alkoxy; amino; $C_1$-$C_4$ aminoalkyl; $C_1$-$C_4$ carbonyloxyl; $C_1$-$C_4$ oxycarbonyl; halogen such as fluorine, chlorine, bromine and iodine; cyano; nitrogen; azido; $C_1$-$C_4$ alkylsulfonyl; thiol; $C_1$-$C_4$ alkylthio; aryloxyl such as phenoxyl; —$NR_b(C=NR_b)NR_b$, $R_c$, where $R_b$ and $R_c$ are independently selected from the group formed by H, $C_1$-$C_4$ alkyl, $C_2$-$C_4$ alkenyl, $C_2$-$C_4$ alkynyl, $C_3$-$C_{10}$ cycloalkyl, $C_6$-$C_{18}$ aryl, $C_7$-$C_{17}$ aralkyl, 3-10 member heterocyclyl or a protecting group of the amino group.

Compounds of the Invention

The compounds of the invention are defined by the general formula (I)

$$R_1\text{-}AA_1\text{-}AA_2\text{-}AA_3\text{-}AA_4\text{-}R_2 \qquad (I)$$

their stereoisomers, mixtures thereof, or their cosmetically or pharmaceutically acceptable salts, characterized in that:
  $AA_1$ is selected from the group formed by -Lys-, -Orn-, -Dab-, -Dpr-, -Agl-, -3,4-dehydrolysine and -4,5-dehydrolysine;
  $AA_2$ is -Ala-;
  $AA_3$ is selected from the group consisting of -Asp-, -Ala-, -Asn-, -Glu- and -Pro-;
  $AA_4$ is -His-;
  $R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO; and
  $R_2$ is selected from the group consisting of —$NR_3R_4$, —$OR_3$ and —$SR_3$;

where $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl and substituted or unsubstituted aralkyl;
  where $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl.

The $R_1$ and $R_2$ groups are bound to the amino-terminal (N-terminal) and carboxy-terminal (C-terminal) ends of the peptide sequences respectively.

According to a preferred embodiment of this invention, $R_1$ is selected from the group consisting of H or $R_5$—CO—, where $R_5$ is selected from the group consisting of substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_5$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members and substituted or unsubstituted heteroarylalkyl with 2 to 24 carbon atoms and 1 to 3 atoms other than carbon and an alkyl chain of 1 to 6 carbon atoms. More preferably, $R_1$ is selected from H, acetyl, tert-butanoyl, hexanoyl, 2 methylhexanoyl, cyclohexancarboxyl, octanoyl, decanoyl, lauroyl, myristoyl, palmitoyl, stearoyl, oleoyl and linoleoyl. Even more preferably, $R_1$ is selected from H, acetyl, lauroyl, or palmitoyl myristoyl. In an even more preferred embodiment, the radical R1 is H.

According to another preferred embodiment, $R_2$ is —$NR_3R_4$, —$OR_3$ or —$SR_3$, where $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_5$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members and substituted or unsubstituted heteroarylalkyl with 2 to 24 carbon atoms and 1 to 3 atoms other than carbon and an alkyl chain of 1 to 6 carbon atoms. Optionally, $R_3$ and $R_4$ can be bound by means of a carbon-carbon bond, saturated or unsaturated, forming a cycle with the nitrogen atom. More preferably, $R_2$ is —$NR_3R_4$ or —$OR_3$, where $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{10}$ cycloalkyl, substituted or unsubstituted $C_6$-$C_{15}$ aryl and substituted or unsubstituted heterocyclyl with 3-10 ring members, and substituted or unsubstituted heteroarylalkyl with 3 to 10 members and an alkyl chain with 1 to 6 carbon atoms. More preferably $R_3$ and $R_4$ are selected from the group consisting of H, methyl, ethyl, hexyl, dodecyl or hexadecyl. Even more preferably $R_3$ is H and $R_4$ is selected from the group formed by H, methyl, ethyl, hexyl, dodecyl or hexadecyl. According to a more preferred embodiment, $R_2$ is selected from —OH and —$NH_2$.

According to another embodiment of the invention $AA_1$ is -Dpr- and $AA_3$ is selected from the group consisting of -Ala- and -Pro-.

According to another embodiment of this invention, $R_1$ is selected from the group formed by H, acetyl, lauroyl, myristoyl or palmitoyl, $AA_1$ is -L-Dpr-, $AA_2$ is -D-Ala-, $AA_3$ is -L-Ala-, $AA_4$ is -L-His- and $R_2$ is —$NR_3R_4$ or —$OR_3$ where $R_3$ and $R_4$ are independently selected from H, methyl, ethyl, hexyl, dodecyl and hexadecyl, preferably $R_2$ is —OH or —$NH_2$. Even more preferably, $R_1$ is H and $R_2$ is —$NH_2$.

According to another embodiment of this invention, $R_1$ is selected from the group formed by H, acetyl, lauroyl, myristoyl or palmitoyl, $AA_1$ is -L-Dpr-, $AA_2$ is -D-Ala-, $AA_3$ is -L-Pro-, $AA_4$ is -L-His- and $R_2$ is —$NR_3R_4$ or —$OR_3$ where $R_3$ and $R_4$ are independently selected from H, methyl, ethyl, hexyl, dodecyl and hexadecyl, preferably $R_2$ is —OH or —$NH_2$. Even more preferably, $R_1$ is H and $R_2$ is —OH.

According to another embodiment of this invention, $R_1$ is selected from the group formed by H, acetyl, lauroyl, myristoyl or palmitoyl, $AA_1$ is -L-Dpr-, $AA_2$ is -L-Ala-, $AA_3$ is -L-Pro-, $AA_4$ is -L-His- and $R_2$ is —$NR_3R_4$ or —$OR_3$ where $R_3$ and $R_4$ are independently selected from H, methyl, ethyl, hexyl, dodecyl and hexadecyl, preferably $R_2$ is —OH or —$NH_2$. Even more preferably, $R_1$ is H and $R_2$ is —OH.

Preferably, the compounds of formula (I) selected from the group consisting of:

```
H-Dpr-Ala-Ala-His-OH,

H-Dpr-Ala-Ala-His-NH2,

H-Dpr-Ala-Asn-His-OH,

H-Dpr-Ala-Asn-His-NH2,

H-Dpr-Ala-Asp-His-OH,

H-Dpr-Ala-Asp-His-NH2,

H-Dpr-Ala-Glu-His-OH,

H-Dpr-Ala-Glu-His-NH2,

H-Dpr-Ala-Pro-His-OH,

H-Dpr-Ala-Pro-His-NH2,

Palm-Dpr-Ala-Ala-His-OH,

Palm-Dpr-Ala-Ala-His-NH2,

Palm-Dpr-Ala-Asn-His-OH,

Palm-Dpr-Ala-Asn-His-NH2,

Palm-Dpr-Ala-Asp-His-OH,

Palm-Dpr-Ala-Asp-His-NH2,

Palm-Dpr-Ala-Glu-His-OH,

Palm-Dpr-Ala-Glu-His-NH2,

Palm-Dpr-Ala-Pro-His-OH,

Palm-Dpr-Ala-Pro-His-NH2,

H-Orn-Ala-Pro-His-OH,

H-Lys-Ala-Pro-His-OH,

H-Dab-Ala-Pro-His-OH,

H-Agl-Ala-Pro-His-OH,

H-Orn-Ala-Ala-His-OH,

H-Lys-Ala-Ala-His-OH,

H-Dab-Ala-Ala-His-OH,

H-Agl-Ala-Ala-His-OH,

H-Dpr-Ala-Pro-His-CONH-(CH2)15-CH3,

H-Dpr-Ala-Ala-His-CONH-(CH2)15-CH3,

H-4,5-dehydroLys-Ala-Pro-His-OH,

H-3,4-dehydroLys-Ala-Pro-His-OH,

Ac-Dpr-Ala-Pro-His-OH,
and
Ac-Dpr-Ala-Ala-His-OH;
``` their stereoisomers, mixtures thereof or their cosmetically or pharmaceutically acceptable salts.

The peptides of this invention can exist as stereoisomers or mixtures of stereoisomers, for example, the amino acids that forming them can have L-, D-configuration, or be racemic independently of one another. It is therefore possible to obtain isomeric mixtures as well as racemic mixtures or diastereomeric mixtures, or pure diastereomers or enantiomers, depending on the number of asymmetric carbons and which isomers or isomeric mixtures are present. The preferred structures of the peptides of the invention are pure isomers, i.e., enantiomers or diastereomers.

For example, when it is indicated that $AA_1$ can be -Dpr-, it is understood that $AA_1$ is selected from -L-Dpr-, -D-Dpr- or mixtures of both, racemic or non racemic. Equally, when it is said that $AA_2$ can be -Ala-, it is understood that it can be -L-Ala-, -D-Ala- or mixtures of both, racemic or non racemic. The preparation processes described herein allow the person skilled in the art to obtain each of the stereoisomers of the peptides of the invention by choosing the amino acid with the appropriate configuration.

The scope of this invention also includes cosmetically or pharmaceutically acceptable salts of the peptides provided by this invention. The term "cosmetically or pharmaceutically acceptable salts" means a salt admitted for its use in animals and more particularly in humans, and includes the salts used to form base addition salts, either inorganic, such as and without limitation thereto, lithium, sodium, potassium, calcium, magnesium, manganese, copper, zinc or aluminum, inter alia, or organic such as, without limitation thereto, ethylamine, diethylamine, ethylenediamine, ethanolamine, diethanolamine, arginine, lysine, histidine or piperazine inter alia, or acid addition salts, either organic, for example and without limitation thereto, acetate, citrate, lactate, malonate, maleate, tartrate, fumarate, benzoate, aspartate, glutamate, succinate, oleate, trifluoroacetate, oxalate, pamoate or gluconate inter alia, or inorganic, such as for example and without limitation thereto, chloride, sulfate, borate or carbonate inter alia. The nature of the salt is not critical, provided it is cosmetically or pharmaceutically acceptable. The cosmetically or pharmaceutically acceptable salts of the peptides of the invention can be obtained by conventional methods well known in the prior art [S M Berge, L D Bighley and Monkhouse D. C. (1977) *"Pharmaceutical Salts" J. Pharm. Sci* 66:1-19].

Another aspect of this invention refers to a peptide with general formula (I), its stereoisomers, mixtures thereof, or its cosmetically or pharmaceutically acceptable salts, as described in this invention, for the treatment and/or care of skin, mucous membranes, scalp and/or hair.

In one aspect in particular, this invention relates to a peptide with general formula (I) its stereoisomers, mixtures thereof, or its cosmetically or pharmaceutically acceptable salts, as described in this invention, for the treatment and/or care of those conditions, disorders and/or pathologies of the skin, mucous membranes, scalp and/or hair which are the result of the generation of reactive carbonyl species (RCS), in particular the RCS that are generated in the skin, mucous membranes, scalp and/or hair.

In one aspect in particular, this invention relates to a peptide with general formula (I), its stereoisomers, mixtures thereof, or its cosmetically or pharmaceutically acceptable salts, as described in this invention, for the scavenging of RCS, preferably for the scavenging of the RCS that are generated in the skin, mucous membranes, scalp and/or hair.

In one aspect in particular, the treatment and/or care of this invention consists of photoprotection, protection of cell DNA and/or repair of the cell DNA of skin, mucous membranes, scalp and/or hair.

In one aspect in particular, the treatment and/or care of this invention, is performed by topical or transdermal application; preferably, the topical or transdermal application is performed by iontophoresis, sonophoresis, electroporation, mechanical pressure, osmotic pressure gradient, occlusive treatment, microinjections, needle-free injections by means of pressure, by means of microelectric patches or any combination thereof.

In another aspect, more particularly, the treatment and/or care is done by oral administration.

In another aspect in particular, this invention relates to a peptide with general formula (I), its stereoisomers, mixtures thereof, or its cosmetically or pharmaceutically acceptable salts, as described in this invention, for the treatment and/or care of skin, mucous membranes, scalp and/or hair with the objective of reducing, postponing and/or preventing signs of aging, photoaging, cellulite and/or body odor.

In another aspect in particular, this invention relates to a peptide with general formula (I), its stereoisomers, mixtures thereof, or its cosmetically or pharmaceutically acceptable salts, as described in this invention, for hair treatment or hair hygiene.

In another aspect in particular, this invention relates to a peptide with general formula (I), its stereoisomers, mixtures thereof, or its cosmetically or pharmaceutically acceptable salts, as described in this invention, for the treatment and/or care of body skin or for body hygiene.

Process of Preparation

The synthesis of the peptides of the invention, their stereoisomers or their cosmetically or pharmaceutically acceptable salts, can be performed according to conventional methods known in the prior art, e.g. by methods of solid phase peptide synthesis [Stewart J M and Young J. D. (1984) "*Solid Phase Peptide Synthesis,* 2nd edition" Pierce Chemical Company, Rockford, Ill.; Bodanzsky M. and Bodanzsky A. (1984) "*The practice of Peptide Synthesis*" Springer Verlag, N.Y., Lloyd Williams P., Albericio F. and Giralt E. (1997) "*Chemical Approaches to the Synthesis of Peptides and Proteins*" CRC, Boca Raton, Fla., USA], synthesis in solution, a combination of methods for solid phase synthesis and enzymatic synthesis solution or [Kullmann W. (1980) "*Proteases as catalysts for enzymic syntheses of opioid peptides*" J. Biol. Chem. 255:8234-8238]. The peptides can also be obtained by fermentation of a bacterial strain, genetically engineered or not, in order to produce the desired sequences, or by controlled hydrolysis of animal or plant proteins, preferably plant, to release peptide fragments containing at least the desired sequence.

For example, a method for obtaining the peptides of the invention of formula (I) comprises the steps of:
coupling of an amino acid with the N-terminal end protected and the C-terminal end free, on an amino acid with the N-terminal end free and the C-terminal end protected or bound to a solid support;
elimination of the protecting group of the N-terminal end;
repetition of the sequence of coupling and removal of the protecting group of the N-terminal to obtain the desired peptide sequence;
elimination of the protecting group of the C-terminal end or cleavage from the solid support.

Preferably, the C-terminal end is bound to a solid support and the process is conducted in solid phase and therefore includes the coupling of an amino acid with the N-terminal end protected and the C-terminal end free on an amino acid with the N-terminal end free and the C-terminal end bound to a polymer support, elimination of the protecting group of the N-terminal end; and repetition of this sequence as many times as necessary to obtain a tetrapeptide, followed finally by the cleavage of the peptide synthesized from the original polymer support.

The functional groups of the side chains of amino acids remain adequately protected with temporary or permanent protecting groups during synthesis and can be deprotected simultaneously or orthogonally to the process of cleavage of the peptide from the polymer support.

Alternatively, the solid phase synthesis can be performed by a convergent strategy coupling a dipeptide or a tripeptide on the polymer support or a dipeptide or amino acid previously linked to the polymer support. Convergent synthesis strategies are widely known by experts and are described in Lloyd Williams P., Albericio F. and Giralt E. on "*Convergent solid phase peptide synthesis*" (1993) *Tetrahedron* 49:11065-11133.

The process may comprise the additional steps of deprotection of the N-terminal end and C-terminal end and/or cleavage of the peptide in indistinct order from the polymer support using standard conditions and processes known in the art, after which they may change the functional groups such extremes. Optional modification of the N-terminal end and C-terminal end can be performed with the peptide with formula (I) anchored to the polymer support or after the peptide has been cleaved from the polymer support.

Alternatively, $R_1$ may be introduced by the reaction of the N-terminal end of the peptide of the invention with a compound $R_1$—X, where $R_1$ has the meaning described above and X is a leaving group such as and without limitation thereto, the tosyl group, the mesyl group and halogen groups inter alia; by nucleophilic substitution reaction in the presence of a base and suitable solvent and where the fragments have functional groups not involved in N—C bond formation adequately protected with temporary or permanent protecting groups.

Optionally and/or additionally, $R_2$ radicals may be introduced by the reaction of a compound $HR_2$ where $R_2$ is —$OR_3$, —$NR_3R_4$ or —$SR_3$, with an additional fragment corresponding to the peptide with formula (I) in which $R_2$ is —OH in the presence of a suitable solvent and a base such as for example N,N-diisopropylethylamine or triethylamine or an additive such as 1-hydroxybenzotriazole (HOBt) or 1-hidroxiazabenzotriazol (HOAt) and a dehydrating agent, such as for example a carbodiimide, an uronium salt, a phosphonium salt or amidinium salt, inter alia, or by prior formation of an acyl halide with, for example, thionyl chloride, and thereby obtain a peptide according to the invention with general formula (I), where the fragments have functional groups not involved in the N—C bond formation, adequately protected with temporary or permanent protecting groups, or alternatively other $R_2$ radicals may be introduced by simultaneous incorporation of the peptide cleavage process from the polymer support.

An expert on the subject will readily understand that the stages of deprotection/cleavage of the C-terminal end and N-terminal end and subsequent derivatization can be performed in indistinct order, according to processes known in the art [Smith, M. B. and March, J. (1999) *"March's Advanced Organic Chemistry Reactions, Mechanisms and Structure"*, 5th Edition, John Wiley & Sons, 2001].

The term "protecting group" refers to a group that blocks an organic functional group and which can be eliminated under controlled conditions. Protecting groups, their relative reactivities and the conditions under which they remain inert are known to an expert on the subject.

Representative examples of protecting groups for the amino group are amides, such as amide acetate, amide benzoate, amide pivalate; carbamates such as benzyloxycarbonyl (Cbz or Z), 2-chlorobenzyl (ClZ) para-nitrobenzyloxycarbonyl (pNZ), tert-butyloxycarbonyl (Boc), 2,2,2-trichloroethoxycarbonyl (Troc), 2-(trimethylsilyl)ethyloxycarbonyl (Teoc), 9-fluorenylmethyloxycarbonyl (Fmoc) or allyloxycarbonyl (Alloc), Trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxo-cyclohexylidene)-3-methyl-butyl (ivDde), 1-(1-adamantyl)-1-methylethoxy-carbonyl (Adpoc), inter alia, preferably Boc or Fmoc.

Representative examples of protecting groups for carboxyl-esters such as tert-butyl ester (tBu), allyl ester (All), triphenylmethyl ester (trityl ester, Trt), cyclohexyl ester (cHx), benzyl ester (Bzl), ortho-nitrobenzyl ester, para-nitrobenzyl ester, para-methoxybenzyl ester, trimethylsilylethynyl ester, 2-phenylisopropyl ester, fluorenylmethyl ester (Fm), 4-(N-[1 - (4,4-dimethyl-2,6-dioxocyclohexylidene)-3-methylbutyl]amino) benzyl ester (Dmab), inter alia; preferred protecting groups of the invention are the esters of All, tBu, cHex, Bzl and Trt.

Trifunctional amino acids can be protected during the synthetic process with temporary or permanent orthogonal protecting groups to the protecting groups of the N-terminal end and C-terminal end.

For the protection of the amino group of lysine side chains, ornithine, diaminobutyric acid, diaminopropionic acid, aminoglycine, 3,4-dehydrolysine and 4,5-dehydrolysine amides can be employed, such as amide acetate, amide benzoate, amide pivalate, carbamates such as benzyloxycarbonyl (Cbz or Z), 2-chlorobenzyl (ClZ) para-nitrobenzyl oxycarbonyl (pNZ), tert-butyloxycarbonyl (Boc), 2,2,2-trichloroethoxycarbonyl (Troc), 2-(trimethylsilyl) ethyloxycarbonyl (Teocar), 9-fluorenylmethyloxycarbonyl (Fmoc) or allyloxycarbonyl (Alloc), Trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxo-cyclohexyliden)-3-methyl-butyl (ivDde), 1-(4,4-dimethyl-2,6-dioxo-cyclohexylidene)-3-methyl-butyl (ivDde), 1-(1-adamantyl)-1-methyl ethoxy-carbonyl (Adpoc), inter alia. For the protection of the carboxyl group of the side chains of aspartic and glutamic acid, esters can be employed, such as tert-butyl ester (tBu), allyl ester (All), triphenylmethyl ester (trityl ester, Trt), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm) 4-(N-[1-(4,4-dimethyl-2,6-dioxo cyclohexylidene)-3-methylbutyl]amino) benzyl (Dmab), inter alia. The histidine imidazolyl group can be protected with the tosyl group (Tos), tert-butyloxycarbonyl group (Boc), benzyl group (Bzl), benzyloxymethyl group (Bom), Trityl (Trt) group, methyltrityl (Mtt) group, 2-mesitylenesulfonyl (Mts) group or 2,4-dinitrophenyl (Dnp), inter alia, and the asparagine amide group can be protected with the Trityl (Trt) group, the methyltrityl (Mtt) group or the xantyl (Xan) group or used without protection of the amide group.

In a preferred embodiment, the strategy of protecting groups used is the strategy where the amino groups are protected by Boc, the carboxyl groups are protected by Bzl, Chex or All, the side chain of asparagine is not protected and histidine is protected with Tos or Dnp.

In another preferred embodiment, the strategy of protecting groups used is the strategy where the amino groups are protected by Fmoc, the carboxyl groups are protected by tBu, All or Trt, the side chain of asparagine is protected by Trt and histidine by Trt or Mtt.

Examples of these and other additional protecting groups, their introduction and their removal can be found in the literature [Greene T W and P G M Wuts, (1999) *"Protective groups in Organic Synthesis"* John Wiley & Sons, New York, Atherton B. and Sheppard R. C. (1989) *"Solid Phase Peptide Synthesis: A practical approach"* IRL Oxford University Press]. The term "protecting groups" also includes polymeric supports used in solid phase synthesis.

When the synthesis takes place wholly or partially in solid phase, it is possible to cite as solid supports for use in the method of the invention, polystyrene supports, polyethyleneglycol grafted on polystyrene and similar, such as, for example, and without limitation thereto, p-methylbenzhydrylamine resins (MBNA) [Matsueda G R and Stewart J. M. (1981) *"A p-methylbenzhydrylamine resin for improved solid phase synthesis of peptide amides"* Peptides 2:45-50], resins 2 chlorotrityl [Barlos K., Gatos D., Kallitsis J. Papaphotiu G., Sotiriu P., Wenqing Y. and W. Schäfer (1989) *"Darstellung geschutzter Peptid substituierter Fragmente unter Einsatz Triphenylmethyl Harze"* Tetrahedron Lett. 30:3943-3946; Barlos K., Gatos D., Kapolos S., Papaphotiu G., Schafer W. and Wenqing Y. (1989) *"Veresterung von partiell geschützten Peptid fragment mit Harz. Einsatz von 2-Chlortritylchlorid zur Synthese von Leu1-Gastrin I"* Tetrahedron Lett. 30:3947-3951] TentaGelâ resins (Rapp Polymere GmbH), ChemMatrix® resins (Matrix Innovation, Inc) and similar, which may or may not include a labile spacer, such as 5-(4-aminomethyl-3,5-dimethoxy-phenoxy)-valeric acid (PAL) [Albericio F., Kneib Cordonier N., Biancalana S., Gera L., Masada R I, Hudson D. and Barany G. (1990) *"Preparation and application of the 5-(4-(9-fluorenylmethyloxycarbonyl)aminomethyl-3,5-dimethoxy-phenoxy)-valeric acid (PAL) handle for the solid phase synthesis of C-terminal peptide amides under mild conditions"* J. Org. Chem 55:3730 3743], the 2-[4-aminomethyl-(2,4-dimethoxyphenyl)]phenoxyacetic acid (AM) [Rink H. (1987) *"Solid phase synthesis of protected peptide fragments using a diphenyl trialkoxy-methylester-resin"* Tetrahedron Lett. 28:3787 3790], Wang [Wang S. S. (1973) *"p-Alkoxybenzyl Alcohol Resin and p Alkoxybenzyloxycarbonylhydrazide Resin for Solid Phase Synthesis of Protected Peptide Fragments"* J. Am. Chem. Soc. 95:1328-1333] and similar, which allow for simultaneous deprotection and peptide cleavage from the polymer support.

Cosmetic or Pharmaceutical Compositions

The peptides of the invention can be administered to capture the RCS by any means that produce contact of the peptides with their site of action in the body of a mammal, preferably human, and in the form of composition that contains them.

In this regard, another aspect of the invention is a cosmetic or pharmaceutical composition comprising at least one peptide with general formula (I), its stereoisomers, mixtures thereof or its cosmetically or pharmaceutically acceptable salts together with at least one cosmetically or pharmaceutically acceptable adjuvant. Such compositions can be prepared by conventional methods known to an expert on the subject ["Harry's Cosmeticology", Eight Edition (2000) Rieger M M, ed., New York Chemical Pub, NY, U.S.; "Remington: The Science and Practice of Pharmacy, Twentieth Edition (2003) Gennaro A R, ed., Lippincott Williams & Wilkins, Philadelphia, U.S.].

The peptides of this invention have variable solubility in water, depending on the nature of their sequence or the possible modifications at the N-terminal end and/or C-terminal end that they have. Therefore, the peptides of this invention can be incorporated into compositions by aqueous solution, and those that are not soluble in water can be solubilized in conventional cosmetically or pharmaceutically acceptable solvents such as for example and without limitation thereto, ethanol, propanol, isopropanol, propylene glycol, glycerin, butylene glycol or polyethylene glycol or any combination thereof.

The cosmetically or pharmaceutically effective amount of the peptides of the invention to be administered, as well as their dosage, will depend on many factors, including the age, condition of the patient, severity of the disorder or pathology, the route and frequency of administration and the particular nature of the peptides to be used.

"Cosmetically or pharmaceutically effective amount" means a non-toxic but sufficient amount of peptide or peptides of the invention to provide the desired effect. The peptides of the invention are used in the cosmetic or pharmaceutical composition of this invention at cosmetically or pharmaceutically effective concentrations to achieve the desired effect; in a preferred form versus the total weight of the composition, between 0.00000001% (by weight) and 20% (by weight), preferably between 0.000001% (by weight) and 20% (by weight), more preferably between 0.0001% (by weight) and 10% (by weight) and even more preferably between 0.0001% (by weight) and 5% (by weight).

The peptides of the invention can also be incorporated in cosmetic or pharmaceutical delivery systems and/or sustained release systems.

The term "delivery systems" refers to a diluent, adjuvant, excipient or carrier with which the peptide of the invention is administered. These cosmetic or pharmaceutical carriers can be liquids such as water, oils or surfactants, including those of petroleum, animal, plant or synthetic origin, for example and without limitation thereto, peanut oil, soybean oil, mineral oil, sesame oil, castor oils, polysorbates, sorbitan esters, ether sulfates, sulfates, betaines, glucosides, maltosides, fatty alcohols, nonoxynols, poloxamers, polyoxyethylenes, polyethylene glycols, dextrose, glycerol, digitonin and similar. In "Remington's Pharmaceutical Sciences" by E. W. Martin there is a description of diluents, adjuvants or excipients as appropriate carriers.

The term "sustained release" is used in the conventional sense referring to a delivery system for a compound that provides the gradual release of the compound for a period of time and preferably, but not necessarily, with constant release levels of the compound throughout a period of time.

Examples of delivery systems or sustained release systems are liposomes, mixed liposomes, oleosomes, milliparticles, microparticles, nanoparticles and solid lipid nanoparticles, sponges, cyclodextrines, vesicles, micelles, mixed micelles of surfactants, surfactant-phospholipid mixed micelles, milliespheres, microspheres and nanospheres, lipospheres, millicapsules, microcapsules and nanocapsules, as well as in microemulsions and nanoemulsions, which can be added to achieve a greater penetration of the active ingredient and/or to improve its pharmacokinetic and pharmacodynamic properties.

Sustained release systems can be prepared by methods known in the prior art, and compositions containing them can be administered, for example, by topical administration, including adhesive patches, non-adhesive patches and microelectric patches or by systemic administration, for example and without limitation thereto, by via oral or parenteral, including nasal, rectal or subcutaneous implantation or injection, or direct implantation or injection into a specific body part, and preferably must release a relatively constant quantity of peptides of the invention. The amount of peptide contained in the sustained release system will depend, for example, on the site of administration, the kinetics and duration of the release of the peptide of the invention, as well as the nature of the condition, disorder and/or pathology to be treated or prevented.

The peptides of this invention may also be adsorbed on solid organic polymers or solid mineral supports such as, for example, and without limitation thereto, talc, bentonite, silica, starch or maltodextrin inter alia.

The compositions containing the peptides of the invention can also be incorporated into fabrics, non-woven fabrics and medical devices that are in direct contact with skin, mucous membranes and/or scalp, so that they release the peptides of the invention either by biodegradation of the anchoring system to the fabric or non-woven fabric or medical device or by friction of the latter with the body, by body moisture, by the pH of the skin or by body temperature. Furthermore, fabrics and non-woven fabrics can be used for making garments that are in direct contact with the body. Preferably, fabrics, non-woven fabrics and medical devices containing the peptides of the invention are used for the treatment and/or care of those conditions, disorders and/or pathologies of the skin, mucous membranes, scalp and/or hair that result from generation of RCS.

Examples of fabrics, non-woven fabrics, garments, medical devices and means of immobilizing peptides to them, including the delivery systems and/or sustained release systems described above can be found in the literature and are known in the state of the art Schaab C. K. (1986) "Impregnating Fabrics With Microcapsules", HAPPI May 1986; Nelson G. (2002) "Application of microencapsulation in textiles" Int J. Pharm. 242:55-62; "Biofunctional Textiles and the Skin" (2006) Curr. Probl. Dermatol. v.33, Hipler U. C. and Elsner P., eds. S. Karger A G, Basel, Switzerland; Malcom R. K.; McCullagh S. D., Woolfson A. D., Gorman S. P., Jones D. S. and Cuddy J. (2004) "Controlled release of a model antibacterial drug from a novel self-lubricating silicone biomaterial" J. Cont. Release 97:313-320]. Preferred fabrics, non-woven fabrics, garments and medical devices are 'bandages, gauze, shirts, socks, stockings, underwear, girdles, gloves, diapers, sanitary towels, dressings, bedspreads, wipes, hydrogels, adhesive patches, non-adhesive patches, microelectric patches and/or facial masks.

The cosmetic and pharmaceutical compositions containing the peptides of this invention, their stereoisomers, mixtures thereof or their cosmetically or pharmaceutically acceptable salts, can be used in different types of compositions topical or transdermal application optionally including cosmetically or pharmaceutically acceptable excipients necessary for formulating the desired dosage form [Faulíi Trillo C. (1993) in "*Tratado de Farmacia Galénica*", Luzán 5, S. A. Ediciones, Madrid].

The compositions for topical or transdermal application may be presented in any solid, liquid or semi-solid formulation, such as for example, and without limitation thereto, creams, multiple emulsions such as, for example, and without limitation thereto, emulsions of oil and/or silicone in water, emulsions of water in oil and/or silicone, emulsions of the water/oil/water type or the water/silicone/water type and emulsions of the oil/water/oil type or silicone/water/silicone type, anhydrous compositions, aqueous dispersions, oils, milks, balsams, foams, lotions, gels, cream gels, hydroalcoholic solutions, hydroglycolic solutions, liniments, sera, soaps, shampoos, conditioners, serums, polysaccharide films, ointments, mousses, pomades, powders, bars, pencils, sprays, including "leave on" formulations and "rinse off" formulations. These formulations for topical or transdermal application can be incorporated using techniques known by the person skilled in the art into different types of solid accessories, such as, for example, and without limitation thereto, wipes, hydrogels, adhesive patches, non-adhesive patches, microelectric patches or facial masks, or can be incorporated into different makeup products such as makeup foundation, for example fluid foundation and compact foundation, makeup removal lotions, makeup removal milks, concealers, eye shadows, lipsticks, lip protectors, lip glosses and powders, inter alia.

The cosmetic or pharmaceutical compositions of the invention may include agents that increase the percutaneous absorption of the peptides of this invention, for example and without limitation thereto, dimethylsulfoxide, dimethylacetamide, dimethylformamide, surfactants, azone (1-dodecylazacycloheptan-2-one), alcohol, urea, ethoxydiglycol, acetone, propylene glycol or polyethylene glycol, inter alia. Furthermore, the cosmetic and pharmaceutical compositions of this invention can be applied to the local areas to be treated by means of iontophoresis, sonophoresis, electroporation, microelectric patches, mechanical pressure, osmotic pressure gradient, occlusive treatment, microinjections or needles-free injections by means of pressure, such as for example injections by oxygen pressure, or any combination thereof, to achieve greater penetration of the peptide of the invention. The area of application will be determined by the nature of the condition, disorder and/or pathology to be prevented or treated.

Furthermore, the cosmetic compositions containing the peptides of this invention, their stereoisomers or their cosmetically or pharmaceutically acceptable salts can be used in different types of formulations for oral administration, preferably in the form of oral cosmetics, for example and without limitation thereto, capsules, including gelatin capsules, tablets, including sugar coated tablets, powders, granulated forms, chewing gum, solutions, suspensions, emulsions, syrups, polysaccharide films, jellies or gelatins, and any other presentation known to an expert on the subject. In particular, the peptides of the invention can be incorporated into any form of functional food or fortified food, such as and without limitation thereto, in dietary bars or compact or noncompact powders. These powders can be solubilized in water, soda, dairy products, soy derivatives or be incorporated into dietary bars. The peptides of this invention may be formulated with common excipients and adjuvants for oral compositions or food supplements, such as and without limitation thereto, fat components, aqueous components, humectants, preservatives, texturizing agents, flavors, aromas, antioxidants and colorants common in the food industry.

The cosmetic and pharmaceutical compositions containing the peptides of the invention, their stereoisomers, mixtures thereof or their cosmetically or pharmaceutically acceptable salts can also be administered by topical or transdermal route, by any other appropriate route, e.g. oral or parenteral route, for which purpose they will include the pharmaceutically acceptable excipients necessary for the formulation of the desired dosage form. In the context of this invention, the term "parenteral" includes the nasal, auricular, ophthalmic, rectal route, subcutaneous injections, intradermal injections, intravascular injections, such as intravenous, intramuscular, intravitreous, intraspinal, intracranial, intraarticular, intrathecal and intraperitoneal injections and any another similar injection or infusion technique. A review of the different pharmaceutical dosage forms of the active ingredients and excipients necessary for obtaining them can be found, for example, in "*Tratado de Farmacia Galénica*" C. Fauli i Trillo, 1993, Luzán 5, S. A. Ediciones, Madrid.

Among the cosmetically or pharmaceutically acceptable adjuvants contained in the cosmetic and pharmaceutical compositions described in this invention are included additional ingredients commonly used in the compositions for the treatment and/or care of the skin, mucous membranes and/or scalp such as, for example, and without limitation thereto, other RCS scavengers, MMP inhibiting agents, melanin synthesis stimulating or inhibiting agents, whitening or depigmenting agents, propigmenting agents, self-tanning agents, antiaging agents, inhibiting agents of NO-synthase, inhibiting agents of $5\alpha$ reductase, inhibitor agents of lysyl-and/or prolyl-hydroxylase, antioxidants, free radical scavengers and/or agents against atmospheric pollution, anti-glycation agents, antihistamine agents, antiemetic agents, antiviral agents, antiparasitic agents, emulsifiers, emollients, organic solvents, liquid propellants, skin conditioners such as humectants, substances that retain moisture, alpha hydroxy acids, beta hydroxy acids, moisturizers, epidermal hydrolytic enzymes, vitamins, pigments or colorants, dyes, gelling polymers, thickeners, surfactants, softening agents, anti-wrinkle agents, agents able to reduce or treat the bags under the eyes, exfoliating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, such as for example agents stimulating the synthesis of collagen, agents stimulating the synthesis of elastin, agents stimulating the synthesis of decorin, agents stimulating the synthesis of laminin, agents stimulating the synthesis of defensins, agents stimulating the synthesis of chaperones, agents stimulating the synthesis of aquaporins, agents stimulating the synthesis of hyaluronic acid, agents stimulating the synthesis of fibronectin, agents stimulating the synthesis of sirtuins, agents stimulating the synthesis of lipids and components of the stratum corneum (ceramides, fatty acids, etc.), other agents that inhibit collagen degradation, agents that inhibit elastin degradation, agents that inhibit serine proteases such as leukocyte elastase or cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, agents stimulating the synthesis of glycosaminoglycans, antihyperkeratosis agents, comedolytic agents, antipsoriasis agents, DNA repairing agents, DNA-protecting agents, stabilizers, anti-itching agents, agents for the treatment and/or care of sensitive skin, firming agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism agents to improve dermal-epidermal junction, agents inducing hair growth, hair growth inhibiting or retardant agents, preservatives, perfumes, chelating agents, plant extracts, essential oils, marine extracts, agents obtained from a biofermentation process, mineral salts, cell extracts and sunscreens (organic or mineral photoprotection agents active against A and/or B ultraviolet rays) inter alia, provided they are physically and chemically compatible with the other components of the composition, and especially with the peptides with general formula (I) contained in the composition of this invention. Furthermore, the nature of these additional ingredients should not unacceptably alter the benefits of the peptides of this invention. The nature of these additional ingredients can be synthetic or natural, such as plant extracts, or can come from a biofermentation process. Additional examples can be found described in the *CTFA International Cosmetic Ingredient Dictionary & Handbook,* 12th Edition (2008).

An additional aspect of this invention relates to a cosmetic or pharmaceutical composition containing a cosmetically or pharmaceutically effective amount of at least one peptide of the invention, its stereoisomers, mixtures thereof or its cosmetically or pharmaceutically acceptable salts, and furthermore a cosmetically or pharmaceutically effective amount of at least one synthetic or natural compound, natural extract or product obtained by a biofermentation process which is a Reactive Carbonyl Species scavenger, free radical scavenger and/or anti-glycation agent, such as, for example, and without limitation thereto, carnosine and its derivatives, GHK [INCI: Tripeptide-1] and its salts and/or derivatives, or Aldenine® [INCI: Hydrolized wheat protein, hydrolized soy protein, Tripeptide-1] marketed by Lipotec, inter alia.

An additional aspect of this invention relates to a cosmetic or pharmaceutical composition including a cosmetically or pharmaceutically effective amount of at least one peptide according to the general formula (I), its stereoisomers, mixtures thereof or its cosmetically or pharmaceutically acceptable salts, and also a cosmetically or pharmaceutically effective amount of at least one extract which is an anti-wrinkle agent and/or anti-aging agent, for example and without limitation thereto, extracts of *Vitis vinifera, Rosa canina, Curcuma longa, Iris pallida, Theobroma cacao, Ginkgo biloba, Leontopodium Alpinum* or *Dunaliella salina* inter alia, or at least one synthetic compound or biofermentation product that is an anti-wrinkle or anti-aging agent, for example and without limitation thereto, Matrixyl® [INCI: Palmitoyl Pentapeptide-3] or Matrixyl 3000® [INCI: Palmitoyl Tetrapeptide-3 Palmitoyl Oligopeptide] marketed by Sederma, Vialox® [INCI: Pentapeptide-3], Syn-ake® [INCI: Dipeptide Diaminobutyroyl Benzylamide Diacetate] or Preregen® [INCI: Glycine Soja (Soybean) Protein, Oxido Reductases] marketed by Pentapharm/DSM, Myoxinol™ [INCI: Hydrolyzed Hibiscus Esculentus Extract] or DN-AGE™ LS [INCI: Cassia Alata leaf Extract] marketed by Laboratoires Sérobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Aldenine® [INCI: Hydrolized wheat protein, hydrolized soy protein, Tripeptide-1] Trylagen™ [INCI: Pseudoalteromonas Ferment Extract, Hydrolyzed Wheat Protein, Hydrolyzed Soy Protein, Tripeptide-10 Citrulline, Tripeptide-1]; Eyeseryl® [INCI: Acetyl Tetrapeptide-5], Lipochroman-6 [INCI: Dimethylmethoxy Chromanol], Chromabright™ [INCI: Dimethylmethoxy Chromanyl Palmitate] or Antarcticine® [INCI: Pseudoalteromonas Ferment Extract] marketed by Lipotec, Kollaren® [INCI: Tripeptide-1, Dextran] marketed by Institut Europeen de Biologie Cellulaire, Collaxyl® IS [INCI: Hexapeptide-9], Orsirtine™ GL [INCI: *Oryza Sativa* (Rice) Extract], D'Orientine™ IS [INCI: Phoenix Dactylifera (Date) Seed Extract] Phytoquintescine™ [INCI: Einkorn (Triticum monococcum) Extract] or Quintescine™ IS [INCI: Dipeptide-4] marketed by Vincience, BONT-L-Peptide [proposed INCI: Palmitoyl Hexapeptide] marketed by Infinitec Activos, $Ca^{2+}$ channel antagonists such as, for example and without limitation thereto, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repairing enzymes such as, for example and without limitation thereto, photolyase or T4 endonuclease V, or chloride channel agonists inter alia.

An additional aspect of this invention refers to a cosmetic or pharmaceutical composition that includes at least a cosmetically or pharmaceutically effective amount of at least one peptide according to the general formula (I), its stereoisomers, mixtures thereof or its cosmetically or pharmaceutically acceptable salts, and furthermore a cosmetically or pharmaceutically effective amount of at least one synthetic or natural extract which is an anti-cellulite agent, lipolytic agent and/or venotonic agent such as for example, and without limitation thereto, extracts or hydrolysates of extracts of *Bupleurum Chinensis, Cecropia Obtusifolia, Celosia Cristata, Centella Asiatica, Chenopodium Quinoa, Chrysanthellum Indicum, Citrus Aurantium Amara, Coffea Arabica, Coleus Forskohlii, Commiphora Myrrha, Crithmum Maritimum, Eugenia Caryophyllus, Ginkgo Biloba, Hedera Helix* (ivy extract), *Hibiscus Sabdariffa, Ilex Paraguariensis, Laminaria Digitata, Nelumbium Speciosum, Paullinia Cupana, Peumus Boldus, Phyllacantha Fibrosa, Prunella Vulgaris, Prunus Amygdalus Dulcis, Ruscus Aculeatus* (butcher's broom extract), *Sambucus Nigra, Spirulina Platensis Algae, Uncaria Tomentosa* or *Verbena Officinalis* inter alia, or, in addition, at least a synthetic compound, biofermentation extract or product that is an anti-cellulite agent, lipolytic agent and/or venotonic agent, for example and without limitation thereto, dihydromyricetin, coenzyme A, lipase, glaucin, esculin, visnadine, Regu®-Shape [INCI: Isomerized Linoleic Acid, Lecithin, Glycerin, Polysorbate 80] marketed by Pentapharm/DSM, UCPeptide™ V [INCI: Pentapeptide] or AT Peptide™ IS [INCI: Tripeptide-3] marketed by Vincience/ISP, Adiposlim [INCI: Sorbitan Laurate, Lauroyl Proline] marketed by SEPPIC, caffeine, carnitine, escin and/or triethanolamine iodide, inter alia.

Applications

Another aspect of this invention relates to the use of at least one of the peptides with general formula (I), their stereoisomers, mixtures thereof or their cosmetically or pharmaceutically acceptable salts in the preparation of a cosmetic or pharmaceutical composition for the treatment and/or care of skin, mucous membranes, scalp and/or hair.

Additionally, this invention relates to the use of at least one of the peptides with general formula (I), their stereoisomers, mixtures thereof or their cosmetically or pharmaceutically acceptable salts in the preparation of a cosmetic or pharmaceutical composition for the scavenging of RCS, preferably RCS generated in the skin, mucous membranes, scalp and/or hair.

Furthermore, another aspect of this invention relates to the use of at least one of the peptides with general formula (I), their stereoisomers, mixtures thereof or their cosmeticaiiy or pharmaceutically acceptable salts in the preparation of a cosmetic or pharmaceutical composition for the treatment and/or care for those conditions, disorders and/or pathologies of the skin, mucous membranes, scalp and/or hair that result from the generation of RCS. Preferably, the cosmetic or pharmaceutical compositions are prepared to treat and/or care for those areas of skin, mucous membranes, scalp and/or hair showing signs of aging, photoaging, cellulite and/or body odor. In an even more preferred manner, the treatment and/or care consists of photoprotection, protection of cell DNA and/or repair of cell DNA of skin, mucous membranes, scalp and/or hair.

Preferably, among the conditions, disorders and/or pathologies of the skin, mucous membranes, scalp and/or hair, to treat and/or care for due to a generation of RCS are aging, photoaging, cellulite and body odor.

Preferably, this invention relates to the use of a peptide with formula (I) in the preparation of a cosmetic or pharmaceutical composition for the treatment of skin, mucous membranes, scalp and/or hair to reduce, postpone and/or prevent the signs of aging and/or of photoaging.

According to another preferred embodiment, this invention relates to the use of at least one of the peptides with general formula (I), their stereoisomers, mixtures thereof, or their cosmetically or pharmaceutically acceptable salts in the preparation of a cosmetic or pharmaceutical composition for hair treatment or hair hygiene. Examples of cosmetic or pharmaceutical composition for hair treatment or hair hygiene include shampoos, conditioners, hair lotions, hair tonics and scalp masks, inter alia.

According to another preferred embodiment, this invention relates to the use of at least one of the peptides with general formula (I), their stereoisomers, mixtures thereof, or their cosmetically or pharmaceutically acceptable salts in the preparation of a cosmetic or pharmaceutical composition for the treatment of the body skin or body hygiene. Examples of cosmetic or pharmaceutical composition for the treatment of the body skin or body hygiene include creams, multiple emulsions such as, for example, and without limitation thereto, emulsions of oil and/or silicone in water, emulsions of water in oil and/or silicone, emulsions of the water/oil/water type or the water/silicone/water type and emulsions of the oil/water/oil type or silicone/water/silicone type, anhydrous compositions, aqueous dispersions, oils, milks, balsams, foams, lotions, gels, gels creams, hydroalcoholic solutions, hydroglycolic solutions, liniments, sera, soaps, serums, polysaccharide films, ointments, mousses, pomades, powders, bars, pencils, sprays or sprays, including "leave on" and "rinse off" formulations, wipes, hydrogels, adhesive patches, non-adhesive patches, microelectric patches or facial masks, makeup line products such as makeup foundations such as fluid and compact foundations, makeup removal lotions, makeup removal milks, concealers, eye shadows, lipsticks, lip protectors, lip glosses and powders, inter alia.

The compositions containing the peptides of this invention, its stereoisomers, mixtures thereof or their cosmetically or pharmaceutically acceptable salts can be applied to the skin, mucous membranes, scalp and/or hair or administered orally or parenterally as necessary to treat and/or care for a condition, disorder and/or pathology.

The cosmetic or pharmaceutical compositions concerned by this invention can be applied to the skin and/or scalp by means of iontophoresis, sonophoresis, electroporation, microelectric patches, mechanical pressure, osmotic pressure gradient, occlusive treatment, microinjections or needle-free injections by means of pressure, such as injections by oxygen pressure, or any combination thereof, to achieve greater penetration of the peptide of the invention.

An additional aspect of this invention relates to a cosmetic or pharmaceutical method for the treatment and/or care for conditions, disorders and/or pathologies of mammals, preferably humans, which benefit from a scavenging of RCS, which comprises administering an effective amount of at least one peptide with general formula (I), its stereoisomers, mixtures thereof or its cosmetically or pharmaceutically acceptable salts, preferably in the form of a cosmetic or pharmaceutical composition containing them. This invention also provides a cosmetic or pharmaceutical method for scavenging RCS, preferably the RCS generated in the skin, mucous membranes, scalp and/or hair.

Moreover, this invention provides a method for the cosmetic or pharmaceutical treatment and/or care for those conditions, disorders and/or pathologies of skin, mucous membranes, scalp and/or hair which are the result of a generation of RCS, including the topical or transdermic application on the skin, mucous membranes, scalp and/or hair or oral or parenteral administration of a cosmetic or pharmaceutical composition containing at least one peptide of the invention, its stereoisomers, mixtures thereof its or cosmetically or pharmaceutically acceptable salts.

The frequency of the application or administration can vary widely, depending on the needs of each subject, with recommendation for a range of application or administration from once a month to ten times a day, preferably from once a week to four times a day, more preferably from three times a week to three times a day, even more preferably once or twice a day.

The following specific examples provided here illustrate the nature of this invention. These examples are included for illustrative purposes only and should not be construed as limitations on the invention claimed herein.

EXAMPLES

General Methodology

All reagents and solvents are of synthesis quality and are used without additional treatment.

Abbreviations

The abbreviations used for amino acids follow the rules of the Commission on Biochemical Nomenclature of the IUPAC-IUB specified in *Eur J. Biochem.* (1984) 138:9-37 and *J. Chem* (1989) 264:633-673.

Ac, acetyl; DNA, deoxyribonucleic acid; Adpoc, 1-(1-adamantyl)-1-methylethoxy-carbonyl; Agl, aminoglycin or diaminoacidic acid; Ala, alanine; All, allyl; Alloc, aliloxycarbonyl; AM, 2-[4 aminomethyl-(2,4-dimethoxyphenyl)] phenoxyacetic acid; Asn, asparagine; Asp, aspartic acid; Boc, tert-butyloxycarbonyl; Bom, benzyloxymethyl; Cbz, benzyloxycarbonyl; cHx, cyclohexyl; ClTrt-®, resin 2-chlorotrityl; CLZ, 2-chlorobenzyl; cps, centipoise; C-terminal, carboxy terminal; Dab, 1,4-diaminobutyric acid; DCM, dichloromethane; Dde, N-[1-(4,4-dimethyl-2,6-dioxocyclohex-1-ylidene) ethyl; DIEA, N,N-diisopropylethylamine; DIPCDI, N,N'-diisopropylcarbodiimide; Dmab, 4-(N-[1-(4,4-dimethyl-2,6-dioxociclohexiliden)-3-methylbutyl]amino)benzyl; DMF, N,N-dimethylformamide; DMSO, dimethylsulfoxide; DNP, 2,4-dinitrophenyl; DPPC, dipalmitoylphosphatidylcholine; Dpr, 1,3-diaminoprop'anoic acid; equiv, equivalent; ESI-MS, electrospray ionization mass spectrometry; Fm, fluorenylmethyl; Fmoc, 9-fluorenylmethyloxycarbonyl; Glu, glutamic acid; His, histidine; HNE, 4-hydroxy-2 nonenal; HOAt, 1-hydroxyazabenzotriazol; HOBt, 1-hydroxybenzotriazol; HPLC, high performance liquid chromatography; INCI, International Nomenclature of Cosmetic Ingredients; ivDde, 1-(4,4-dimethyl-2,6-dioxo-cyclohexyliden)-3-methyl-butyl; Lys, lysine; MBHA, p-methylbenzhydrylamine; MDA, malondialdehyde; MeCN, acetonitrile; MeOH, methanol; MLV, multilaminar vesicles; MMP, matrix metalloproteinase; Mts, 2-mesitylenesulfonyl (Mts); Mtt, methyltrityl or methoxytrityl, NE, 2-nonenal, N-terminal, amino-terminal; Orn, ornithine; PAL, 5-(4-aminomethyl-3,5-dimethoxyphenoxy) valeric acid; Palm, palmitoyl; PBS, phosphate buffer saline; pNZ para-nitrobenzyloxycarbonyl; Pro, proline; RCS, Reactive Carbonyl Species; ®, resin; ROS, Reactive Oxygen Species; tBu, tert-butyl; Teoc, 2-(trimethylsilyl)ethyloxycarbonyl; TFA, trifluoroacetic acid; THF, tetrahydrofuran; TIS triisopropylsilane; Tos, tosyl; Troc, 2,2,2-trichloroethyloxycarbonyl; Trt, Trityl; ULV Unilaminar vesicles; UV, ultraviolet; Xan, xantyl; Z, benzyloxycarbonyl;

Chemical Synthesis

All synthetic processes are carried out in polypropylene syringes equipped with discs of porous polyethylene or Pyrex® reactors equipped with porous plate. Solvents and soluble reagents are removed by suction. The Fmoc group is removed with piperidine-DMF (2:8, v/v) (1×1 min, 1×5 min, 5 mL/g resin) [Lloyd Williams P., Albericio F. and Giralt E. (1997) "Chemical Approaches to the Synthesis of Peptides and Proteins" CRC, Boca Raton, Fla., USA]. Washes between stages of deprotecting, coupling, and, again, deprotecting, were carried out with DMF (3×1 min) each time using 10 mL solvent/g resin. Coupling reactions were performed with 3 mL solvent/g resin. The control of the couplings is done by the ninhydrin test [E. Kaiser, R L Colescott, C D Bossing and Cook P. I. (1970) Color test for detection of free terminal amino groups in the solid phase synthesis of peptides, "Anal. Biochem. 34:595-598] or chloranil [Christensen T. (1979) "A qualitative test for monitoring coupling completeness in solid-phase peptide synthesis using Chloranil" Acta Chem Scand. 338:763-766]. All synthetic transformations and washes were carried out at room temperature.

Example 1

Obtaining Fmoc-AA$_1$-AA$_2$-AA$_3$-AA$_4$-O-2-ClTrt-®.

5.45 g of Fmoc-L-His(Trt)-OH or 5.45 g of Fmoc-D-His (Trt)-OH (8.8 mmol; 1 equiv) were incorporated, dissolved in 55 ml of DCM to which was added 1.3 ml of DIEA (7.6 mmol, 0.86 equiv) over 2 chlorotrityl resin (5.5 g, 8.8 mmol) dry. They were stirred for 5 min, after which 2.5 mL of IDEA (14.6 mmol 1.66 equiv) were added. It was left to react for 40 min. Chloride groups were blocked by treatment with the remaining 4.4 mL of MeOH.

The Fmoc N-terminal end group was deprotected as described in general methods and incorporated on the peptidyl resin 7.25 g of Fmoc-L-Ala-OH, 13.13 g of Fmoc-L-Asn (Trt)-OH, 9.05 g Fmoc-L-Asp(OtBu)-OH, 9.05 g Fmoc-D-Asp(OtBu)-OH, 9.76 g Fmoc-L-Glu(OtBu)-OH and 7.42 g of Fmoc-L-Pro-OH (22 mmol, 2.5 equiv) in the presence of DIPCDI (3.39 mL, 22 mmol, 2.5 equiv) and HOBt (3.37 g; 22 mmol, 2.5 equiv) using DMF as solvent for 1 hour. The resin was then washed as described in general methods and the deprotection treatment of the Fmoc group was repeated to incorporate the next amino acid. According to the protocols described, we coupled sequentially 7.25 g of Fmoc-L-Ala-OH or 7.25 g of Fmoc-D-Ala-OH (22 mmol, 2.5 equiv) and 9.38 g Fmoc-L-Dpr(Boc)-OH, (22 mmol, 2.5 equiv) in the presence, of 3.37 g of HOBt (22 mmol, 2.5 equiv) and 3.39 mL of DIPCDI (22 mmol, 2.5 equiv). In place of 9.38 g Fmoc-L-Dpr(Boc)-OH, 10.31 g of Fmoc-L-Lys(Boc)-OH, 10.00 g of Fmoc-L-Orn(Boc)-OH, 9.69 g Fmoc-L-Dab(Boc)-OH, 9.07 g Fmoc-L-Aql(Boc)-OH, 10.26 g of Fmoc-L-3,4-dehydroLys(Boc)-OH or 10.26 g of Fmoc-L-4,5-dehydroLys (Boc)-OH could have been used.

After the synthesis, the peptidyl resins were washed with DCM (5×3 min) and dried by nitrogen stream.

Example 2

Obtaining Fmoc-AA$_1$-AA$_2$-AA$_3$-AA$_4$-AM-MBHA-®.

6.85 g Fmoc-AM-MBHA resin of functionalization 0.73 mmol/g (5 mmol) were treated with piperidine-DMF according to the general protocol described in order to eliminate the Fmoc group. On the deprotected resin were incorporated 15.49 g of Fmoc-L-His (Trt)-OH or 15.49 g of Fmoc-D-His (Trt)-OH (25 mmol; 5 equiv) in the presence of DIPCDI (3.85 mL, 25 mmol; 5 equiv) and HOBt (3.85 g, 25 mmol; 5 equiv), using DMF as solvent for 1 hour.

The resin was then washed as described in general methods and the deprotection treatment of the Fmoc group was repeated to incorporate the next amino acid. Following the described protocols, they were sequentially coupled 8.23 g of Fmoc-L-Ala-OH, 14.92 g of Fmoc-L-Asn(Trt)-OH, 10.29 g of Fmoc-L-Asp(OtBu)-OH, 10.29 g of Fmoc-D-Asp(OtBu)-OH, 11.09 g of Fmoc-L-Glu(OtBu)-OH or 8.44 g of Fmoc-L-Pro-OH (25 mmol; 5 equiv), 8.23 g Fmoc-L-Ala-OH or 8.23 g of Fmoc-D-Ala-OH (25 mmol; 5 equiv) and 10.66 g of Fmoc-L-Dpr(Boc)-OH, (25 mmol; 5 equiv) in the presence of 3.85 g of HOBt (25 mmol; 5 equiv) and 3.85 mL of DIPCDI (25 mmol: 5 equiv). In place of 10.66 g of Fmoc-L-Dpr(Boc)-OH, 11.72 g of Fmoc-L-Lys(Boc)-OH, 11.36 g of Fmoc-L-Orn(Boc)-OH, 11.01 g of Fmoc-L-Dab(Boc)-OH, 10.31 g of Fmoc-L-Agl(Boc)-OH, 11.67 g of Fmoc-L-3,4-dehydroLys (Boc)-OH, or 11.67 g of Fmoc-L-4,5-dehydroLys (Boc)-OH could have been used.

After the synthesis, the peptidyl resins were washed with DCM (5×3 min) and dried by nitrogen stream.

Example 3

General process for cleaving the N-terminal Fmoc protecting group.

The Fmoc N-terminal end group of the peptidyl resins obtained in Examples 1 and 2 was deprotected as described in general methods (20% piperidine in DMF, 1×5 min+1×20 min). The peptidyl resins were washed with DMF (5×1 min), DCM (4×1 min), diethyl ether (4×1 min) and dried under vacuum.

Example 4

Prophetic

Process for introduction of R$_1$ palmitoyl group: Obtaining Palm-AA$_1$-AA$_2$-AA$_3$-AA$_4$-O-2-ClTrt® and Palm-AA$_1$-AA$_2$-AA$_3$-AA$_4$-AM-MBHA-®.

About 1 mmol of peptidyl resins obtained in Example 3 were added to 2.56 g of palmitic acid (10 mmol; 10 equiv) predissolved in DMF (1 mL) in the presence of 1.53 g of HOBt (10 mmol; 10 equiv) and 1.54 mL DIPCDI (10 mmol;

10 equiv). They were left to react for 15 hours, after which the resin was washed with THF (5×1 min), DCM (5×1 min), DMF (5×1 min), MeOH (5×1 min), DMF (5×1 min) THF (5×1 min), DMF (5×1 min), DCM (4×1 min), ether (3×1 min), and dried under vacuum.

Example 5

Prophetic

Process for introduction of acetyl group $R_1$ Derivation of Ac-$AA_1$-$AA_2$-$AA_3$-$AA_4$-O-2-ClTrt-® and Ac-$AA_1$-$AA_2$-$AA_3$-$AA_4$-AM-MBHA-®.

1 mmol of peptidyl resins obtained in Example 3 was treated with 25 equiv of acetic anhydride in the presence of 25 equiv of IDEA using 5 mL of DMF as solvent. It was left to react for 30 min, after which the peptidyl resins were washed with DMF (5×1 min), DCM (4×1 min), diethyl ether (4×1 min) and dried under vacuum.

Example 6

Process for cleaving from the polymeric support: Obtaining $AA_1$-$AA_2$-$AA_3$-$AA_4$-OH, Ac-$AA_1$-$AA_2$-$AA_3$-$AA_4$-OH, Palm-$AA_1$-$AA_2$-$AA_3$-$AA_4$-OH, H-$AA_1$-$AA_2$-$AA_3$-$AA_4$-$NH_2$, Ac-$AA_1$-$AA_2$-$AA_3$-$AA_4$-$NH_2$ and Palm-$AA_1$-$AA_2$-$AA_3$-$AA_4$-$NH_2$.

200 mg of the dried peptidyl resin obtained in Example 3 was treated with 5 mL of TFA-TIS-$H_2O$ (90:5:5) for 2 hours at room temperature under stirring. Filtrates were collected on 50 mL cold diethyl ether, filtered through polypropylene syringes fitted with porous polyethylene discs and were washed 5 times with 50 mL diethyl ether. The final precipitates were dried under vacuum.

HPLC analysis of peptide obtained in gradients of MeCN (+0.07% TFA) in $H_2O$ (+0.1% TFA) showed a purity exceeding 85%. The identity of the peptide obtained was confirmed by ES-MS.

Example 7

Prophetic

Process for cleaving from the polymeric support and functionalization with $R_2$ substituted amine: Obtaining Ac-$AA_1$-$AA_2$-$AA_3$ $AA_4$-NH—$(CH_2)_{15}CH_3$.

The peptides Ac-$AA_1$-$AA_2$-$AA_3$-$AA_4$-OH with completely protected side chains were obtained by treating 150 mg of peptidyl resin Ac-$AA_1$-$AA_2$-$AA_3$-$AA_4$-O-2-ClTrt-® from Example 6, previously dried under vacuum in the presence of KOH, with a 3 mL 3% solution of TFA in DCM for 5 min. The filtrates were collected on 50 mL of cold diethyl ether and the treatment was repeated three times. The ether solutions were evaporated in vacuum to dryness at room temperature; the precipitates were resuspended in 50% MeCN in $H_2O$ and lyophilized. 10 mg of the obtained crude peptide were weighed in a flask, were added to 3 equiv of hexadecylamine and 25 mL of anhydrous DMF. 2 equiv of DIPCDI were added, and left to react with magnetic stirring at 47° C. Reactions were monitored by HPLC by disappearance of the initial products, which was complete after 24-48 h: Solvents were evaporated to dryness and coevaporated twice with DCM. The residues obtained [Ac-$AA_1$-$AA_2$-$AA_3$-$AA_4$-NH—$(CH_2)_{15}$—$CH_3$ with side chains fully protected] were resuspended in 25 mL of a mixture of TFA-DCM-anisole (49:49:2) and left to react for 30 min at room temperature. They were added to 250 mL of cold diethyl ether, the solvents were evaporated at reduced pressure and two additional coevaporations with ether were carried out. The residues were dissolved in a mixture of 50% MeCN in $H_2O$ and lyophilized.

HPLC analysis of peptides obtained in gradients of MeCN (+0.07% TFA) in $H_2O$ (+0.1% TFA) showed a purity exceeding 70% in all cases. The identity of the peptides obtained was confirmed by ES-MS.

Example 8

Scavenging assay of 4-hydroxy-2-nonenal.

A solution was prepared from peptides in a 10 mM PBS buffer at a concentration of 2 mM, as well as a solution of the aldehyde in acetonitrile at a concentration of 100 μM. Equal volumes of peptide solutions and aldehyde were mixed and were left to react at 37° C. for 24 h. The scavenging efficiency of the RCS was measured by HPLC analysis of the remaining aldehyde content in the reaction mixture.

Table 2 details the peptides that showed levels of HNE aldehyde capture greater than 85%.

TABLE 2

Scavenging percentage of HNE aldehyde

| Peptide | Scavenging % |
|---|---|
| Carnosine | 89.4 |
| GHK | 82.1 |
| H-L-Dpr-D-Ala-L-Asp-L-His-OH | 98.8 |
| H-L-Dpr-D-Ala-L-Pro-L-His-$NH_2$ | 98.3 |
| H-L-Dpr-D-Ala-L-Pro-L-His-OH | 98.0 |
| H-L-Dpr-D-Ala-L-Ala-L-His-$NH_2$ | 97.7 |
| H-L-Dpr-D-Ala-L-Glu-L-His-$NH_2$ | 97.7 |
| H-L-Dpr-L-Ala-L-Asp-L-His-OH | 97.6 |
| H-L-Dpr-L-Ala-L-Asp-L-His-$NH_2$ | 97.5 |
| H-L-Dpr-L-Ala-L-Pro-L-His-$NH_2$ | 96.3 |
| H-L-Dpr-L-Ala-L-Ala-L-His-$NH_2$ | 96.0 |
| H-L-Dpr-L-Ala-D-Asp-L-His-OH | 94.1 |
| H-L-Dpr-L-Ala-L-Pro-L-His-OH | 93.9 |
| H-L-Dpr-L-Ala-L-Asp-D-His-OH | 86.3 |

Example 9

Scavenging assay of 2-nonenal.

A solution was prepared from peptides in a 10 mM PBS buffer at a concentration of 2 mM, as well as a solution of the aldehyde in acetonitrile at a concentration of 100 μM. Equal volumes of peptide solutions and aldehyde were mixed and left to react at 37° C. for 24 h. The scavenging efficiency of the RCS was measured by HPLC analysis of the remaining aldehyde content in the reaction mixture.

Table 3 lists the peptides that showed levels of NE aldehyde capturing greater than 65%.

TABLE 3

Scavenging percentage of NE aldehyde

| Peptide | Scavenging % |
|---|---|
| Carnosine | 70.3 |
| GHK | 24.7 |
| H-L-Dpr-D-Ala-L-Asn-L-His-NH$_2$ | 98.9 |
| H-L-Dpr-D-Ala-L-Ala-L-His-NH$_2$ | 98.2 |
| H-L-Dpr-D-Ala-L-Pro-L-His-NH$_2$ | 98.1 |
| H-L-Dpr-D-Ala-L-Pro-L-His-OH | 97.0 |
| H-L-Dpr-D-Ala-L-Asp-L-His-OH | 95.4 |
| H-L-Dpr-L-Ala-L-Asn-L-His-NH$_2$ | 95.3 |
| H-L-Dpr-D-Ala-L-Glu-L-His-NH$_2$ | 95.2 |
| H-L-Dpr-L-Ala-L-Asp-L-His-NH$_2$ | 94.5 |
| H-L-Dpr-L-Ala-L-Ala-L-His-NH$_2$ | 94.1 |
| H-L-Dpr-D-Ala-L-Glu-L-His-OH | 93.2 |
| H-L-Dpr-L-Ala-L-Glu-L-His-NH$_2$ | 92.6 |
| H-L-Dpr-L-Ala-L-Pro-L-His-NH$_2$ | 88.7 |
| H-L-Dpr-L-Ala-D-Asp-L-His-OH | 83.1 |
| H-L-Dpr-L-Ala-L-Pro-L-His-OH | 76.7 |
| H-L-Dpr-L-Ala-L-Glu-L-His-OH | 75.6 |
| H-L-Dpr-L-Ala-L-Ala-L-His-OH | 74.6 |
| H-L-Dpr-L-Ala-L-Asn-L-His-OH | 73.1 |
| H-L-Dpr-L-Ala-L-Asp-D-His-OH | 66.5 |

Example 10

Testing the photoprotection efficiency of H-L-Dpr-D-Ala-L-Pro-L-His-OH, H-L-Dpr-D-Ala-L-Ala-L-His-OH and H-L-Dp- L-Ala-L-Pro-L-His-OH in cultured human keratinocytes.

Human keratinocytes were maintained in culture for 24 h on 96 well plates to form monolayers and the cells were pre-incubated in the dark with 1 mg/ml of H-L-Dpr-D-Ala-L-Pro-L-His-OH, H-L-Dpr-D-Ala-L-Ala-L-His-OH, H-L-Dpr-L-Ala-L-Pro-L-His-OH or phosphate buffered saline (control) for one hour at 37° C. and humidified air with 5% CO.sub.2. Subsequently, cells were irradiated with a solar simulation lamp (with an energy of 37 J/cm$^2$ at room temperature for 150 min in the case of H-L-Dpr-D-Ala-L-Pro-L-His-OH). A control plate was kept in the dark during the same time at room temperature. After the period of irradiation, the cell medium was replaced by a fresh medium and the cells were incubated for an additional 24 h.

Cell viability was determined by the Neutral Red dye, measuring the absorbance at 540 nm in a spectrophotometer.

The photoprotection efficiency was determined by comparing the viability obtained in cells treated with H-L-Dpr-D-Ala-L-Pro-L-His-OH, H-L-Dpr-D-Ala-L-Ala-L-His-OH or H-L-Dpr-L-Ala-L-Pro-L-His-OH on the response of irradiated and non-irradiated control cells.

TABLE 4

Photoprotection efficiency of the peptides of the invention

| TREATMENT EFFICIENCY | CELLULAR VIABILITY | PHOTO-PROTECTION |
|---|---|---|
| Control | 100% | — |
| Irradiated control | 27.7% | — |
| H-L-Dpr-D-Ala-L-Pro-L-His-OH | 53.1% | 92.0% |
| H-L-Dpr-L-Ala-L-Pro-L-His-OH | 43.4% | 56.8% |

Example 11

Test of the Protective Capacity of DNA Degradation

Primary cultures of human melanocytes ($10^5$ cells/plate) were treated with 1.0 µg/mL of H-L-Dpr-D-Ala-L-Pro-L-His-OH for 2 h at 37° C. Subsequently, the cultures were irradiated with UVA at 1.0 J/cm$^2$ for no longer than 3min at 4° C. and the extent of the damage induced to DNA was determined by alkaline comet assay [De Meo M., Laget M., Castegnaro M. and Dumenil G. (1991) "*Genotoxic activity of potassium permanganate in acidic solutions*" Mutat. Res 260:295-306].

Table 5 shows the values of protective efficiency against DNA degradation determined for H-L-Dpr-D-Ala-L-His-OH.

TABLE 5

Protective efficiency against DNA degradation

| TREATMENT | PROTECTIVE EFFICIENCY |
|---|---|
| H-L-Dpr-D-Ala-L-Pro-L-His-OH | 36.1% |

Example 12

Prophetic

Testing the Repair Capacity of DNA Degradation

Primary cultures of human fibroblasts ($10^5$ cells/plate) were irradiated to 0.4 J/cm$^2$ UVB for 30 seconds. Subsequently, the cultures were treated with 0.25 mg/mL or 0.5 mg/mL of H-L-Dpr-D-Ala-L- Pro-L-His-OH for 3 h at 37° C. and the extent of the damage to DNA was determined by alkaline comet assay.

Table 6 shows the values of repair efficiency of DNA degradation induced by treatments with H-L-Dpr-D-Ala-L-Pro-L-His-OH versus the intrinsic repair efficiency of the cells.

TABLE 6

Repair efficiency of DNA degradation

| TREATMENT | REPAIR EFFICIENCY |
|---|---|
| H-L-Dpr-D-Ala-L-Pro-L-His-OH 0.25 µg/mL | 120% |
| H-L-Dpr-D-Ala-L-Pro-L-His-OH 0.5 µg/mL | 170% |

Example 13

Prophetic

Preparation of a cosmetic composition containing Palm-L-Dpr-Ala-L-Pro-L-His-OH.

The following formulation was prepared as described in this invention:

|   | INGREDIENT (INCI Nomenclature) | % IN WEIGHT |
|---|---|---|
| A | MINERAL OIL | 8.0 |
| A | STEARIC ACID | 2.4 |
| A | CETEARYL ALCOHOL | 1.6 |
| A | BEESWAX | 0.8 |
| B | GLYCERINE | 2.4 |
| B | AQUA (WATER) | 63.4 |
| C | CARBOMER | 0.3 |
| C | TRIETHANOLAMINE | 0.9 |
| D | AQUA (WATER) | 15.0 |
| D | Palm-L-Dpr-D-Ala-L-Pro-L-His-OH (0.01%) | 5.0 |
| D | LECITHIN | 0.4 |

In a sufficiently large reactor, Phase A components were weighed and the mixture was heated to 80° C. to melt the wax. In a vessel suitable for the entire content, Phase B components were weighed and heated to 70° C. Phase A was slowly added to Phase B under intense stirring, and subsequently Phase C was added to the previous mixture under stirring. Once the addition was finished, it was allowed to cool under gentle stirring, and when the mixture was found to be at room temperature, an aqueous solution of Palm-L-Dpr-D-Ala-L-Pro-L-His-OH and lecithin was added, and the pH was homogenized and corrected with triethanolamine.

The pH of the cream obtained was 6.7 and the viscosity was 10,000-15,000 cps (6/50).

Example 14

Prophetic

Preparation of liposomes containing H-L-Dpr-D-Ala-L-Pro-L-His-OH.

Dipalmitoylphosphatidylcholine (DPPC) was weighed and dissolved in chloroform. The solvent was evaporated under vacuum until a thin layer of phospholipid was obtained, and this layer was hydrated by treatment at 55° C. with an aqueous solution of the peptide to the desired concentration (containing Phenonip®), and MLV liposomes were obtained. ULV liposomes were obtained by immersing MLV liposomes in an ultrasonic bath at 55° C. for 8 cycles of 2 min at 5 min intervals. The size of ULV liposomes was reduced by passing them through an extrusion system at high pressure.

| INGREDIENT (INCI Nomenclature) | % IN WEIGHT |
|---|---|
| PHOSPHATIDYLCHOLINE | 4.0 |
| H-L-Dpr-D-Ala-L-Pro-L-His-OH | 0.2 |
| PHENOXYETHANOL, METHYLPARABEN, ETHYLPARABEN, BUTYLPARABEN, PROPYLPARABEN, ISOBUTYLPARABEN | 0.50 |
| AQUA (WATER) | q.s.p. 100 |

Example 15

Composition of a facial cream containing H-L-Dpr-D-Ala-L-Ala-L-His-OH.

Preparation

Mix the ingredients of Phase A and heat to 70° C.

Mix the ingredients of Phase B and heat to 70° C.

Add Phase C to Phase B, stirring with homogenizer (Silverson) for 5 minutes.

To the mixture of the phases and C, slowly add Phase A with homogenization and maintain homogenization for 15 minutes.

Start cooling to 30-35° C. under gentle stirring. At 50° C. add Phase D. Keep stirring. At 35-38° C. add the previously solubilized Phases E and F.

|   | INGREDIENT (INCI Nomenclature) | % IN WEIGHT |
|---|---|---|
| A | BUTYROSPERMUM PARKII | 3.5-4.5 |
| A | CETEARYL ETHYLHEXANOATE | 3-5 |
| A | GLYCERYL STEARATE S.E. | 1.5-2.5 |
| A | SQUALANE | 0.5-1 |
| A | PEG-100 STEARATE | 1 |
| A | POLYSORBATE 60 | 0.30 |
| A | CETYL PALMITATE | 1.5-2.5 |
| A | DIMETHICONE | 2.5-3.5 |
| A | CETEARYL ALCOHOL | 1.5-2.5 |
| A | PALMITIC ACID | 0.5 |
| B | AQUA (WATER) | 2 |
| B | GLYCERIN | 1.5-2.5 |
| B | BUTYLENE GLYCOL | 1-3 |
| B | MANNITOL | 0.5-1.5 |
| B | HYDROGENATED LECITHIN | 0.5-1.5 |
| B | PROPYLENE GLYCOL | 0.5-1.5 |
| C | CARBOMER | 0.4 |
| C | ETHYLHEXYL PALMITATE | 1.5-2.5 |
| D | TROMETHAMINE | 0.4 |
| D | AQUA (WATER) | 1 |
| E | PRESERVATIVES | q.s. |
| F | H-L-Dpr-D-Ala-L-Ala-L-His-OH | 0.10 |
| F | AQUA (WATER) | q.s.p.100 |

Example 16

Prophetic

Preparation of a composition in the form of a liposome gel containing H-L-Dpr-D-Ala-L-Pro-L-His-OH.

The liposomes of example 14 were dispersed in water with preservatives (EDTA, imidazolidinyl urea and Phenonip®) under gentle stirring. Hispagel® 200 was added [INCI: Aqua, glycerin, glyceryl polyacrylate] and stirred gently until a homogeneous mixture was obtained.

| INGREDIENT (INCI Nomenclature) | % IN WEIGHT |
|---|---|
| LIPOSOMES CONTAINING H-L-Dpr-D-Ala-L-Pro-L-His-OH (1%) | 10.00 |
| DISODIUM EDTA | 0.15 |
| IMIDAZOLIDINYL UREA | 0.10 |
| PHENOXYETHANOL, METHYLPARABEN, ETHYLPARABEN, BUTYLPARABEN, PROPYLPARABEN, ISOBUTYLPARABEN | 0.50 |
| AQUA (WATER) | 29.25 |
| AQUA (WATER), GLYCERIN, GLYCERYL POLYACRYLATE | 60.00 |

Example 17

Prophetic

Composition of a body lotion containing H-L-Dpr-L-Ala-L-Pro-L-His-OH.

| | INGREDIENT (INCI Nomenclature) | % IN WEIGHT |
|---|---|---|
| A | CETEARYL ETHYLHEXANOATE | 3-5 |
| A | GLYCERYL STEARATE SE. | 2.5 |
| A | PEG-100 STEARATE | 1 |
| A | SQUALANE | 2 |
| A | DIMETHICONE | 0.5-1 |
| A | CETYL ALCOHOL | 0.4-0.8 |
| B | AQUA (WATER) | 1 |
| B | BUTYLENE GLYCOL | 1-3 |
| B | GLYCERIN | 0.5-2 |
| B | PROPYLENE GLYCOL | 0.5-1.5 |
| C | CARBOMER | 0.2 |
| C | ETHYLHEXYL PALMITATE | 0.5-1.5 |
| C | ACRYLATES/C10-30 ALKYL ACRYLATE CROSSPOLYMER | 0.1 |
| D | AQUA (WATER) | 1 |
| D | TROMETHAMINE | 0.25 |
| E | PRESERVATIVES | q.s. |
| F | H-L-Dpr-L-Ala-L-Pro-L-His-OH | 0.10 |
| F | AQUA (WATER) | q.s.p. 100 |

Preparation

Mix the ingredients of Phase A and heat to 70° C.

Mix the ingredients of Phase B and heat to 70° C.

Add Phase C to Phase B, stirring with homogenizer (Silverson) for 5 minutes.

To the mixture of phases B and C, gradually add Phase A with homogenizer and maintain homogenization for 15 minutes.

Start cooling to 30-35° C. under gentle stirring. At 50° C. add Phase D. Keep stirring. At 35-38° C. add previously solubilized Phases E and F.

Example 18

Prophetic

Composition of a hair lotion containing H-L-Dpr-D-Ala-L-Ala-L-His-CONH—(CH—CH$_3$.

| | INGREDIENT (INCI Nomenclature) | % IN WEIGHT |
|---|---|---|
| A | DENAT. ALCOHOL | 50-60 |
| A | PANTHENOL | 0.05-0.15 |
| A | ZINC RICINOLEATE | 0.05-0.10 |
| A | FRAGRANCE | 0.02 |
| B | AQUA (WATER) | q.s.p.100 |
| B | H-L-Dpr-D-Ala-L-Ala-L-His-CONH—(CH$_2$)$_{15}$—CH$_3$ | 0.01 |

Preparation:

Mix the ingredients of Phase A.

Mix the ingredients of Phase B.

Slowly add Phase B to Phase A under stirring until complete homogenization.

Example 19

Prophetic

Reduction of the Odor Emitted by Aldehyde 2-nonenal

We evaluated the reduction of the odor given off by aldehyde 2-nonenal after the addition of a solution containing 0.05% of H-L-Dpr-L-Ala-L-Ala-L-His-OH through an olfactory test ("sniff test") conducted by a panel of 3 independent experts.

We prepared a solution of 2-nonenal at 0.00089% in acetonitrile to which was added an equal volume of phosphate buffer 10 mM pH 7-7.5 or H-L-Dpr-L-Ala-L-Ala-L-His-OH to 0.05% in phosphate buffer 10 mM pH 7-7.5. We evaluated the odor intensity given off at time zero and 24 h after creating the mixture of aldehyde and peptide, performing the measurements in a room heated to 24° C. and with controlled humidity at 60% and statistically analyzed the values obtained using the Wilcoxon Matched Paired test.

The peptide H-L-Dpr-L-Ala-L-Ala-L-His-OH was able to reduce the odor given off by 2-nonenal by 15.6%.

The invention claimed is:

1. A peptide with general formula (I)

$$R_1\text{-}AA_2\text{-}AA_3\text{-}AA_4\text{-}R_2 \quad (I)$$

its stereoisomers, mixtures thereof, or its cosmetically or its pharmaceutically acceptable salts comprising:

$AA_1$ is selected from the group consisting of -Lys-, -Orn-, -Dab-, -Dpr-, -Agl-, -3,4-dehydrolysine and -4,5-dehydrolysine;

$AA_2$ is -Ala-;

$AA_3$ is selected from the group consisting of -Asp-, -Ala-, -Asn-, -Glu- and -Pro-;

$AA_4$ is -His-;

$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—; and $R_2$ is selected from the group consisting of —$NR_3R_4$, —$OR_3$ and —$SR_3$;

where $R_3$ and $R_4$ are independently selected from the group consisting of H, unsubstituted noncyclic aliphatic group, substituted or unsubstituted alicycyl, unsubstituted heterocyclyl, unsubstituted heteroarylalkyl, substituted or unsubstituted aryl, and unsubstituted aralkyl; and where $R_5$ is selected from the group consisting of H, substituted or unsubstituted noncyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl, and wherein when $R_1$ or $R_5$ is a substituted non-cyclic aliphatic group, each substituent of said substituted non-cyclic aliphatic group is selected from the group consisting of hydroxyl, $C_1$-$C_4$ alcoxyl, $C_1$-$C_4$ oxycarbonyl, halogen, cyano, nitro, azido, $C_1$-$C_4$ alkylsulfonyl, thiol, alkylthio, aryloxyl, and -$NR_b$(C=$NR_b$)$NR_bR_c$, where $R_b$ and $R_c$ are independently selected from the group consisting of H, $C_1$-$C_4$ alkyl, $C_2$-$C_4$ alkenyl, $C_2$-$C_4$ alkynyl, $C_3$-$C_{10}$ cycloalkyl, $C_6$-$C_{18}$ aryl, $C_7$-$C_{17}$ aralkyl, and 3-10-membered-heterocyclyl.

2. The peptide of claim 1, wherein $R_1$ is selected from the group consisting of H, or $R_5$—CO where $R_5$ is selected from the group consisting of substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_5$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members and substituted or unsubstituted heteroarylalkyl with 2 to 24 carbon atoms and 1 to 3 atoms other than carbon and an alkyl chain of 1 to 6 carbon atoms.

3. The peptide of claim 2, wherein $R_1$ is selected from the group consisting of H, acetyl, tent-butanoyl, hexanoyl, 2-methylhexanonyl, cyclohexancarboxyl, octanoyl, decanoyl, lauroyl, myristoyl, palmitoyl, stearoyl, oleoyl and linoleoyl.

4. The peptide of claim 1, wherein $R_2$ is —$NR_3R_4$ or —$OR_3$, where $R_3$ and $R_4$ are independently selected from the group consisting of H-unsubstituted $C_1$-$C_{24}$ alkyl, unsubstituted $C_2$-$C_{24}$ alkenyl, substituted or unsubstituted $C_3$-$C_{24}$ cycloalkyl, substituted or unsubstituted $C_5$-$C_{24}$ cycloalkenyl, substituted or unsubstituted $C_5$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl with 3-10 ring members and substituted or unsubstituted heteroarylalkyl with 2 to 24 carbon atoms and 1 to 3 atoms other than carbon and an alkyl chain of 1 to 6 carbon atoms.

5. The peptide of claim 4, wherein $R_3$ and $R_4$ are independently selected from the group consisting of H, methyl, ethyl, hexyl, dodecyl and hexadecyl.

6. The peptide of claim 1, wherein $R_1$ is H, acetyl, lauroyl, myristoyl or palmitoyl, $AA_1$, is -L-Dpr-, $AA_2$ is -D-Ala-, $AA_3$ is -L-Ala-, $AA_4$ is -L-His, and $R_2$ is —$NR_3R_4$ or —$OR_3$ where $R_3$ and $R_4$ are independently selected from H, methyl, ethyl, hexyl, dodecyl and hexadecyl.

7. The peptide of claim 1, wherein $R_1$ is H, acetyl, lauroyl, myristoyl or palmitoyl, $AA_1$ is -L-Dpr-, $AA_2$ is -D-Ala-, $AA_3$ is -L-Pro-, $AA_4$ is -L-His, and $R_2$ is -$NR_3R_4$ or -$OR_3$ where $R_3$ and $R_4$ are independently selected from H, methyl, ethyl, hexyl, dodecyl and hexadecyl.

8. The Peptido peptide of claim 1, wherein $R_1$ is H, acetyl, lauroyl, mytistoyl or palmitoyl, $AA_1$ is -L-Dpr-, $AA_2$ is -L-Ala-, $AA_3$ is -L-Pro-, $AA_4$ is -L-His-, and $R_2$ is —$NR_3R_4$ or —$OR_3$ where $R_3$ and $R_4$ are independently selected from H, methyl, ethyl, hexyl, dodecyl and hexadecyl.

9. A process for preparation of a peptide with general formula (1), its stereoisomers, mixtures thereof, or its cosmetically or its pharmaceutically acceptable salts according to claim 1, wherein the peptide is synthesized in solid phase or in solution phase.

10. A cosmetic or pharmaceutical composition comprising at least one peptide with general formula (1), its stereoisomers, mixtures thereof or its cosmetically or pharmaceutically acceptable salts, according to claim 1, and at least one cosmetically or pharmaceutically acceptable excipient or agent other than said peptide.

11. The composition of claim 10, wherein the peptide with general formula (1) is at a concentration of between 0.000001% and 20% in weight, with respect to the total weight of the composition.

12. The composition of claim 10, wherein the peptide with general formula (1), its stereoisomers, mixtures thereof or its cosmetically or pharmaceutically acceptable salts, is incorporated into a delivery system or a cosmetic or pharmaceutically acceptable sustained release system selected from the group consisting of liposomes, mixed liposomes, oleosomes, millicapsules, microcapsules, nanocapsules, sponges, cyclodextrines, vesicles, micelles, mixed micelles of surfactants, surfactant-phospholipid mixed micelles, milliespheres, microspheres, nanospheres, liposheres, micro emulsions, nanoemulsions, milliparticles, microparticles, nanoparticles and solid lipid nanoparticles and/or is adsorbed on a cosmetic or pharmaceutically acceptable solid organic polymer or solid support selected from the group consisting of talc, bentonite, silica, starch and maltodextrin.

13. The composition of claim 10, wherein the composition is in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, liniments, sera, soaps, shampoos, conditioners, serums, ointments, mousses, pomades, powders, bars, pencils, sprays, capsules, gelatin capsules, tablets, sugar coated tablets, granulated forms, chewing gum, solutions, suspensions, emulsions, syrups, polysaccharide films, jelly and gelatin.

14. The composition of claim 10, wherein the composition is incorporated into a product selected from the group consisting of concealers, makeup foundations, makeup removal lotions, makeup removal milks, eye shadows, lipsticks, lip glosses, lip protectors and powders.

15. The composition of claim 10, wherein the peptide with general formula (1), its stereoisomers, mixtures thereof or cosmetically or pharmaceutically acceptable salts is incorporated in a fabric, a nonwoven fabric or a medical device.

16. The composition of claim 10, comprising said at least one agent, the agent being selected from the group consisting of other RCS scavengers, MMP inhibiting agents, melanin synthesis stimulating or inhibiting agents, whitening or depigmenting agents, propigmenting agents, self-tanning agents, antiaging agents, inhibiting agents of NO-synthase, inhibiting agents of 5α reductase, inhibitor agents of lysyl- and/or prolyl-hydroxylase, antioxidants, free radical scavengers and/or agents against atmospheric pollution, anti-glycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, pigments or colorants, dyes, gelling polymers, thickeners, surfactants, softening agents, anti-wrinkle agents, agents able to reduce or treat the bags under the eyes, exfoliating agents, antimicrobial agents, antifungal agents, fungistatic agents, bactericidal agents, bacteriostatic agents, agents stimulating the synthesis of collagen, agents stimulating the synthesis of elastin, agents stimulating the synthesis of decorin, agents stimulating the synthesis of laminin, agents stimulating the synthesis of defensins, agents stimulating the synthesis of chaperones, agents stimulating the synthesis of aquaporins, agents stimulating the synthesis of hyaluronic acid, agents stimulating the synthesis of fibronectin, agents stimulating the synthesis of sirtuins, agents stimulating the synthesis of lipids and components of the stratum corneum, agents that inhibit collagen degradation, agents that inhibit elastin degradation, agents that inhibit serine proteases such as leukocyte elastase or cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, agents stimulating the synthesis of glycosaminoglycans, anti-hyperkeratosis agents, comedolytic agents, antpsoriasis agents, DNA repairing agents, DNA protecting agents, stabilizers, anti-itching agents, agents for the treatment and/or care of sensitive skin, firming agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, preservatives, perfumes, chelating agents, plant extracts, essential oils, marine extracts, agents obtained from a biofermentation process, mineral salts, cell extracts and sunscreens, organic or mineral photoprotection agents active against ultraviolet A and/or B rays, and mixtures thereof.

17. A method for the treatment and/or care of skin, mucous membranes, scalp and/or hair, wherein the treatment and/or care provides photoprotection and/or protection of cell DNA of skin, mucous membranes, scalp and/or hair, the method comprising administering a peptide with general formula (I), $$R_1\text{-}AA_1\text{-}AA_2\text{-}AA_3\text{-}AA_4\text{-}R_2 \text{ (I)}$$

its stereoisomers, mixtures thereof, or its cosmetically or its pharmaceutically acceptable salts to skin, mucous membranes, scalp and/or hair, wherein:

$AA_1$ is selected from the group consisting of -Lys-, -Orn-, -Dab-, -Dpr-, -Agl-, -3,4-dehydrolysine and -4,5-dehydrolysine;

$AA_2$ is -Ala-;

$AA_3$ is selected from the group consisting of -Asp-, -Ala-, -Asn-, -Glu- and -Pro-;

$AA_4$ is -His-;

$R_1$ is selected from the group consisting of H, substituted or unsubstituted non-cyclic aliphatic group, substituted or unsubstituted alicyclyl, substituted or unsubstituted heterocyclyl, substituted or unsubstituted hetero aryl alkyl, substituted or unsubstituted aryl, substituted or unsubstituted aralkyl and $R_5$—CO—; and $R_2$ is selected from the group consisting of —$NR_3R_4$, —$OR_3$ and —$SR_3$;

where $R_3$ and $R_4$ are independently selected from the group consisting of H, substituted or unsubstituted non-cyclic aliphatic group, substituted or unsubstituted alicycyl, substituted or unsubstituted heterocyclyl, substituted or unsubstituted heteroarylalkyl, substituted or unsubstituted aryl, and substituted or unsubstituted aralkyl;

where $R_5$ is selected from the group consisting of H, substituted or unsubstituted noncyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl.

18. A method for the treatment and/or care of skin, mucous membranes, scalp and/or hair, wherein the treatment and/or care reduces and/or postpones signs of aging, photoaging, cellulite and/or body odor, the method comprising administering a peptide with general formula (I), $$R_1\text{-}AA_1\text{-}AA_2\text{-}AA_3\text{-}AA_4\text{-}R_2 \text{ (I)}$$

its stereoisomers, mixtures thereof, or its cosmetically or its pharmaceutically acceptable salts to skin, mucous membranes, scalp and/or hair, wherein:

$AA_1$ is selected from the group consisting of -Lys-, -Orn-, -Dab-, -Dpr-, -Agl-, -3,4-dehydrolysine and -4,5-dehydrolysine;

$AA_2$ is -Ala-;

$AA_3$ is selected from the group consisting of -Asp-, -Ala-, -Asn-, -Glu- and -Pro-; $AA_4$ is -His-;

$R_1$ is selected from the group consisting of H, substituted or unsubstituted non-cyclic aliphatic group, substituted or unsubstituted alicyclyl, substituted or unsubstituted heterocyclyl, substituted or unsubstituted hetero aryl alkyl, substituted or unsubstituted aryl, substituted or unsubstituted aralkyl and $R_5$—CO—; and $R_2$ is selected from the group consisting of —$NR_3R_4$, —$OR_3$ and —$SR_3$;

where $R_3$ and $R_4$ are independently selected from the group consisting of H, substituted or unsubstituted non-cyclic aliphatic group, substituted or unsubstituted alicycyl, substituted or unsubstituted heterocyclyl, substituted or unsubstituted heteroarylalkyl, substituted or unsubstituted aryl, and substituted or unsubstituted aralkyl;

where $R_5$ is selected from the group consisting of H, substituted or unsubstituted noncyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl.

* * * * *

UNITED STATES PATENT AND TRADEMARK OFFICE
CERTIFICATE OF CORRECTION

PATENT NO. : 8,710,010 B2  Page 1 of 1
APPLICATION NO. : 13/122435
DATED : April 29, 2014
INVENTOR(S) : Van Den Nest et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this
Twenty-ninth Day of September, 2015

Michelle K. Lee
*Director of the United States Patent and Trademark Office*